(12) United States Patent
Sadowsky et al.

(10) Patent No.: US 10,286,012 B2
(45) Date of Patent: *May 14, 2019

(54) COMPOSITIONS AND METHODS FOR TRANSPLANTATION OF COLON MICROBIOTA

(71) Applicant: Regents of the University of Minnesota, Minneapolis, MN (US)

(72) Inventors: Michael J. Sadowsky, Roseville, MN (US); Alexander Khoruts, Golden Valley, MN (US); Alexa R. Weingarden, St. Paul, MN (US); Matthew J. Hamilton, Burnsville, MN (US)

(73) Assignee: Regents of the University of Minnesota, Minneapolis, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 15/594,319

(22) Filed: May 12, 2017

(65) Prior Publication Data

US 2017/0246214 A1 Aug. 31, 2017

Related U.S. Application Data

(63) Continuation of application No. 15/261,319, filed on Sep. 9, 2016, now Pat. No. 9,649,343, which is a continuation of application No. 14/003,411, filed as application No. PCT/US2012/028484 on Mar. 9, 2012, now Pat. No. 9,968,638, application No. 15/594,319, which is a continuation of application No. 15/173,134, filed on Jun. 3, 2016, now Pat. No. 10,028,980, which is a continuation of application No. 14/003,411.

(60) Provisional application No. 61/450,838, filed on Mar. 9, 2011.

(51) Int. Cl.

| A61K 35/38 | (2015.01) |
| A61K 35/74 | (2015.01) |
| A61K 45/06 | (2006.01) |
| A61K 9/19 | (2006.01) |
| A61K 35/37 | (2015.01) |
| A61K 35/24 | (2015.01) |
| A61K 35/741 | (2015.01) |
| A61K 9/00 | (2006.01) |
| A61K 35/742 | (2015.01) |
| A61K 9/16 | (2006.01) |
| A61K 47/08 | (2006.01) |
| A61K 47/26 | (2006.01) |
| A61K 35/00 | (2006.01) |

(52) U.S. Cl.
CPC ............ *A61K 35/37* (2013.01); *A61K 9/0053* (2013.01); *A61K 9/16* (2013.01); *A61K 9/1617* (2013.01); *A61K 9/1623* (2013.01); *A61K 35/24* (2013.01); *A61K 35/74* (2013.01); *A61K 35/741* (2013.01); *A61K 35/742* (2013.01); *A61K 45/06* (2013.01); *A61K 47/08* (2013.01); *A61K 47/26* (2013.01); *A61K 2035/11* (2013.01); *Y02A 50/473* (2018.01); *Y02A 50/475* (2018.01)

(58) Field of Classification Search
None
See application file for complete search history.

(56) References Cited

U.S. PATENT DOCUMENTS

| 3,192,116 A | 6/1965 | Möse et al. |
| 3,320,130 A | 5/1967 | Henry |
| 3,713,836 A | 1/1973 | Crlsson |
| 4,098,728 A | 7/1978 | Rosenblatt |
| 4,332,790 A | 6/1982 | Sozzi et al. |
| 4,335,107 A | 6/1982 | Snoeyenbos et al. |
| 4,452,779 A | 6/1984 | Cockerill |
| 4,536,409 A | 8/1985 | Farrell et al. |
| 4,657,762 A | 4/1987 | Mikkola et al. |
| 4,710,379 A | 12/1987 | Kawai et al. |
| 4,892,731 A | 1/1990 | Arai et al. |
| 4,975,286 A | 12/1990 | Hechter |
| 5,213,807 A | 5/1993 | Chemburkar et al. |
| 5,266,315 A | 11/1993 | Taguchi et al. |
| 5,443,826 A | 8/1995 | Borody |
| 5,599,795 A | 2/1997 | McCann et al. |
| 5,728,380 A | 3/1998 | Allen et al. |
| 5,800,821 A | 9/1998 | Acheson et al. |
| 5,837,238 A | 11/1998 | Casas et al. |
| 5,858,356 A | 1/1999 | Wolf et al. |
| 5,902,578 A | 5/1999 | Halpin-Dohnalek et al. |

(Continued)

FOREIGN PATENT DOCUMENTS

| AU | 2001276160 B2 | 6/2007 |
| CA | 1333564 | 12/1994 |

(Continued)

OTHER PUBLICATIONS

Manichanh, et al. 2010. Genome Research, vol. 20, pp. 1411 to 1419. (Year: 2010).*
"Autoimmune Disease List," American Autoimmune Related Diseases Association, pp. 1-4 (2017) <https://www.aarda.org/disease-list/>.
Crohn's Disease, Prevention, Health Guide A-Z, WebMDHealth, pp. 1-2, n.d., Web, Oct. 23, 2005 <http://mywebmd.com/hw/inflammatory.sub.--bowel/uf6012.asp>.
"Certain infectious and parasitic diseases (A00-B99)," International Statistical Classification of Diseases and Related Health Problems, 10th Revision (ICD-10)-WHO Version, Chapter 1, pp. 1 (2016) <www.apps.who.int/classifications/icd10/browse/2016/en#/I>.

(Continued)

*Primary Examiner* — Robert J Yamasaki

(74) *Attorney, Agent, or Firm* — Arnold & Porter Kaye Scholer LLP; David Marsh

(57) ABSTRACT

The present invention provides compositions that include an extract of human feces, and methods for using such compositions, including methods for replacing or supplementing or modifying a subject's colon microbiota, and methods for treating a disease, pathological condition, and/or iatrogenic condition of the colon.

20 Claims, 3 Drawing Sheets

(56) References Cited

U.S. PATENT DOCUMENTS

| | | |
|---|---|---|
| 5,902,743 A | 5/1999 | Luchansky et al. |
| 6,087,386 A | 7/2000 | Chen et al. |
| 6,162,464 A | 12/2000 | Jacob et al. |
| 6,245,740 B1 | 6/2001 | Goldenberg et al. |
| 6,284,274 B1 | 9/2001 | Merrill et al. |
| 6,428,783 B1 | 8/2002 | Khachatrian et al. |
| 6,479,051 B1 | 11/2002 | Bruce |
| 6,514,531 B1 | 2/2003 | Alaux et al. |
| 6,645,530 B1 | 11/2003 | Borody |
| 6,649,397 B1 | 11/2003 | Nakamura |
| 6,756,032 B1 | 6/2004 | Tepper et al. |
| 6,926,907 B2 | 8/2005 | Plachetka |
| 6,979,674 B1 | 12/2005 | Goldenberg et al. |
| 6,984,513 B2 | 1/2006 | Brown et al. |
| 7,018,629 B2 | 3/2006 | Jacob et al. |
| 7,374,753 B1 | 5/2008 | Farmer et al. |
| 7,541,091 B2 | 6/2009 | Sisson et al. |
| 7,749,509 B2 | 7/2010 | Cobb et al. |
| 7,763,276 B1 | 7/2010 | Shodai et al. |
| 7,799,341 B2 | 9/2010 | Porzio et al. |
| 7,815,956 B2 | 10/2010 | Lee et al. |
| 7,846,475 B2 | 12/2010 | Shiraishi et al. |
| 7,888,062 B1 | 2/2011 | Garner et al. |
| 7,998,510 B2 | 8/2011 | Caswell |
| 8,168,171 B2 | 5/2012 | Mogna et al. |
| 8,460,648 B2 | 6/2013 | Borody |
| 8,637,297 B2 | 1/2014 | Fernandez et al. |
| 8,658,153 B2 | 2/2014 | Daube et al. |
| 8,771,673 B2 | 7/2014 | Cobb et al. |
| 9,040,036 B2 | 5/2015 | Borody |
| 9,050,358 B2 | 6/2015 | Borody |
| 9,308,226 B2 | 4/2016 | Borody |
| 9,320,763 B2 | 4/2016 | Borody |
| 9,408,872 B2 | 8/2016 | Borody |
| 9,468,658 B2 | 10/2016 | Borody |
| 9,572,841 B2 | 2/2017 | Borody |
| 9,572,842 B2 | 2/2017 | Borody |
| 9,610,308 B2 | 4/2017 | Borody |
| 9,623,056 B2 | 4/2017 | Borody |
| 2001/0014322 A1 | 8/2001 | Chen et al. |
| 2002/0013270 A1 | 1/2002 | Bolte |
| 2002/0022019 A1 | 2/2002 | Laulund |
| 2002/0039599 A1 | 4/2002 | Lin et al. |
| 2003/0092163 A1 | 5/2003 | Collins et al. |
| 2003/0092724 A1 | 5/2003 | Kao et al. |
| 2003/0147858 A1 | 8/2003 | Renaud et al. |
| 2004/0062757 A1 | 4/2004 | Finegold |
| 2004/0167062 A1 | 8/2004 | Bolte |
| 2004/0170617 A1 | 9/2004 | Finegold |
| 2004/0223956 A1 | 11/2004 | Naidu et al. |
| 2006/0076536 A1 | 4/2006 | Barshied |
| 2006/0099197 A1 | 5/2006 | Farmer |
| 2006/0115465 A1 | 6/2006 | Macfarlane et al. |
| 2006/0177424 A1 | 8/2006 | Cobb et al. |
| 2006/0275223 A1 | 12/2006 | Burr |
| 2007/0059296 A1 | 3/2007 | Chen |
| 2008/0254009 A1 | 10/2008 | Finegold |
| 2008/0299197 A1 | 12/2008 | Toneguzzo et al. |
| 2010/0112003 A1 | 5/2010 | Collins et al. |
| 2010/0178349 A1 | 7/2010 | Kolter et al. |
| 2010/0178413 A1 | 7/2010 | Gorris |
| 2010/0184785 A1 | 7/2010 | Kolter et al. |
| 2010/0222311 A1 | 9/2010 | Thommes et al. |
| 2010/0226866 A1 | 9/2010 | Yamashiro et al. |
| 2010/0233278 A1 | 9/2010 | Ookawa et al. |
| 2010/0239667 A1 | 9/2010 | Hemmingsen et al. |
| 2010/0247489 A1 | 9/2010 | Saur-Brosch et al. |
| 2010/0247665 A1 | 9/2010 | Takahashi |
| 2010/0255231 A1 | 10/2010 | Chau et al. |
| 2010/0255307 A1 | 10/2010 | Gonze et al. |
| 2010/0278930 A1 | 11/2010 | Okumura et al. |
| 2010/0285164 A1 | 11/2010 | Schaible et al. |
| 2010/0289164 A1 | 11/2010 | Porzio et al. |
| 2010/0297031 A1 | 11/2010 | Ubeda Perez et al. |
| 2011/0008554 A1 | 1/2011 | Chen et al. |
| 2011/0045222 A1 | 2/2011 | Peters |
| 2011/0081320 A1 | 4/2011 | Westall et al. |
| 2011/0200570 A1 | 8/2011 | Mosbaugh et al. |
| 2011/0218216 A1 | 9/2011 | Vivek et al. |
| 2012/0039853 A1 | 2/2012 | Corveleyn et al. |
| 2012/0064133 A1 | 3/2012 | Chauhan et al. |
| 2012/0087895 A1 | 4/2012 | Mazmanian et al. |
| 2012/0183612 A1 | 7/2012 | Brogmann et al. |
| 2012/0252775 A1 | 10/2012 | Finegold |
| 2013/0045274 A1 | 2/2013 | Hlavka |
| 2013/0195804 A1 | 8/2013 | Borody |
| 2013/0259899 A1 | 10/2013 | Allen-Vercoe et al. |
| 2013/0316394 A1 | 11/2013 | Stimpson |
| 2014/0065132 A1 | 3/2014 | Hsiao et al. |
| 2014/0086877 A1 | 3/2014 | Hlavka |
| 2014/0147417 A1 | 5/2014 | Sadowsky et al. |
| 2014/0147425 A1 | 5/2014 | Henn et al. |
| 2014/0234260 A1 | 8/2014 | Borody |
| 2014/0255351 A1 | 9/2014 | Berstad et al. |
| 2014/0328803 A1 | 11/2014 | McKenzie et al. |
| 2014/0341921 A1 | 11/2014 | Honda et al. |
| 2014/0342438 A1 | 11/2014 | Allen-Vercoe et al. |
| 2014/0363397 A1 | 12/2014 | Allen-Vercoe et al. |
| 2015/0050246 A1 | 2/2015 | Jones et al. |
| 2015/0093360 A1 | 4/2015 | McKenzie et al. |
| 2015/0143557 A1 | 5/2015 | Honda et al. |
| 2015/0152484 A1 | 6/2015 | Krajmalnik-Brown et al. |
| 2015/0190435 A1 | 7/2015 | Henn et al. |
| 2015/0224152 A1 | 8/2015 | Littman et al. |
| 2015/0238545 A1 | 8/2015 | Borody |
| 2015/0238546 A1 | 8/2015 | Borody |
| 2015/0297642 A1 | 10/2015 | Borody |
| 2015/0306144 A1 | 10/2015 | Borody |
| 2015/0306155 A1 | 10/2015 | Borody |
| 2015/0306156 A1 | 10/2015 | Borody |
| 2015/0374761 A1 | 12/2015 | Sadowsky et al. |
| 2016/0089363 A1 | 3/2016 | Borody |
| 2016/0151429 A1 | 6/2016 | Borody |
| 2016/0151431 A1 | 6/2016 | Borody |
| 2016/0151432 A1 | 6/2016 | Borody |
| 2016/0151433 A1 | 6/2016 | Borody |
| 2016/0158294 A1 | 6/2016 | Von Maltzahn et al. |
| 2016/0279178 A1 | 9/2016 | Borody |
| 2016/0279179 A1 | 9/2016 | Borody |

FOREIGN PATENT DOCUMENTS

| | | |
|---|---|---|
| CA | 2 391 422 A1 | 1/2004 |
| CN | 1561387 A | 1/2005 |
| CN | 201441672 U | 4/2010 |
| DE | 2 134 179 A1 | 1/1973 |
| EP | 0 303 426 A2 | 2/1989 |
| EP | 0 456 418 A2 | 11/1991 |
| EP | 0 433 299 B1 | 5/1998 |
| EP | 1 514 572 A2 | 3/2005 |
| EP | 1 514 572 A3 | 11/2006 |
| EP | 1 800 688 A1 | 6/2007 |
| EP | 1 514 572 B1 | 12/2008 |
| FR | 1275 M | 5/1962 |
| FR | 2427 M | 3/1964 |
| FR | 2828 M | 10/1964 |
| FR | 5528 M | 11/1967 |
| FR | 2 244 464 A1 | 4/1975 |
| GB | 1 271 674 A | 4/1972 |
| JP | 64-67192 | 3/1989 |
| JP | H05-306221 A | 11/1993 |
| JP | H07-242539 A | 9/1995 |
| JP | H07-242557 A | 9/1995 |
| JP | 3 144 556 B2 | 3/2001 |
| JP | 2004-501095 | 1/2004 |
| JP | 2005-118544 A | 5/2005 |
| JP | 2008-106066 | 5/2008 |
| JP | 2010-513359 | 4/2010 |
| JP | 2010-520234 A | 6/2010 |
| WO | WO 90/01335 A1 | 2/1990 |
| WO | WO 95/33046 A1 | 12/1995 |
| WO | WO 96/11014 A1 | 4/1996 |
| WO | WO 98/13068 A1 | 4/1998 |
| WO | WO 00/07571 A2 | 2/2000 |

(56) References Cited

FOREIGN PATENT DOCUMENTS

| WO | WO 00/015760 | 3/2000 |
|---|---|---|
| WO | WO 00/42168 A2 | 7/2000 |
| WO | WO 02/07741 A1 | 1/2002 |
| WO | WO 03/033681 A2 | 4/2003 |
| WO | WO 2005/017095 A2 | 2/2005 |
| WO | WO 2006/127355 A2 | 11/2006 |
| WO | WO 2008/077614 A2 | 7/2008 |
| WO | WO 2008/105715 A2 | 9/2008 |
| WO | WO 2008/117266 A2 | 10/2008 |
| WO | WO 2008/117267 A2 | 10/2008 |
| WO | WO 2008/077614 A3 | 1/2009 |
| WO | WO 2009/026306 A2 | 2/2009 |
| WO | WO 2009/055362 A1 | 4/2009 |
| WO | WO 2010/040020 A1 | 4/2010 |
| WO | WO 2011/033310 A1 | 3/2011 |
| WO | WO 2011/094027 A1 | 8/2011 |
| WO | WO 2011/110347 A2 | 9/2011 |
| WO | WO 2011/151941 A1 | 12/2011 |
| WO | WO 2011/152566 A2 | 12/2011 |
| WO | WO 2012/016287 A2 | 2/2012 |
| WO | WO 2012/045150 A1 | 4/2012 |
| WO | WO 2012/122478 A1 | 9/2012 |
| WO | WO 2012/016287 A3 | 11/2012 |
| WO | WO 2013/037067 A1 | 3/2013 |
| WO | WO 2013/090825 A1 | 6/2013 |
| WO | WO 2014/078911 A1 | 5/2014 |
| WO | WO 2014/152338 A1 | 9/2014 |
| WO | WO 2014/152484 A1 | 9/2014 |
| WO | WO 2015/006355 A2 | 1/2015 |
| WO | WO 2015/051323 A1 | 4/2015 |
| WO | WO 2015/077794 A1 | 5/2015 |
| WO | WO 2015/095241 A2 | 6/2015 |
| WO | WO 2016/183577 A1 | 11/2016 |
| WO | WO 2016/191356 A1 | 12/2016 |
| WO | WO 2017/075098 A1 | 5/2017 |
| WO | WO 2017/152137 A2 | 9/2017 |

OTHER PUBLICATIONS

"Spore-Forming Gram-Positive Bacilli: Bacillus and Clostridium Species," Jawetz, Melnick, & Adelberg's Medical Microbiology, 26th Edition, Chapter 11, pp. 1-15 (2012).

"ARGF—'Autologous Rehabilitation of Gastrointestinal Flora,'" Medipex Report for Medilink NW, pp. 1-42, n.d., Web, Feb. 10, 2012 <http://www.bacteriotherapy.org/docs/medipex-report.pdf>.

"Frequently Asked Questions about Clostridium difficile for Healthcare Providers," Healthcare-associated Infections (HAIs), Centers for Disease Control and Prevention, pp. 1-6, Nov. 25, 2010, updated Mar. 6, 2012, Web, May 19, 2014 <http://www.cdc.gov/HAI/organisms/cdiff/Cdiff_faqs_HCP.html>.

"Functional Anatomy of Prokaryotic and Eukaryotic Cells," printed Mar. 16, 2017 <http://classes.midlandstech.edu/carterp/courses/bio225/chap04/lecture2.htm>.

"Monilia," Def. 1, Stedman's Medical Dictionary, n.d., Web, Nov. 22, 2005.

"Probiotic," Def. 1, MSN Encarta—Dictionary, Encarta, n.d., Web, Dec. 1, 2005.

Aas et al., "Recurrent Clostridium difficile Colitis: Case Series Involving 18 Patients Treated with Donor Stool Administered via a Nasogastric Tube," Clinical Infectious Diseases, 36(5):580-585 (2003).

Abrams, "Open-Label, Uncontrolled Trial of Bowel Sterilization and Repopulation with Normal Bowel Flora for Treatment of Inflammatory Bowel Disease," Current Therapeutic Research, 58(12):1001-1012 (1997).

Acha et al., "Changes of viability and composition of the *Escherichia coli* flora in faecal samples during long time storage," Journal of Microbiological Methods, Elsevier, 63(3):229-238 (2005).

Agrawal et al., "'Global warming' to *Mycobacterium avium* subspecies paratuberculosis," Future Microbiol, 9(7):829-832 (2014).

Agrawal et al., "A Long-Term Follow-Up Study of the Efficacy and Safety of Fecal Microbiota Transplant (FMT) for Recurrent/Severe/Complicated C. difficile Infection (CDI) in the Elderly," Gastroenterol, 146(5)(Suppl 1):542-43 (2014).

Aitken et al., "Demonstration of Intracellular *Mycobacterium* Species in Crohn's Disease Using Novel Technologies," Poster Presentation—2015 ACG Annual Scientific Meeting, Honolulu, Hawaii, USA (2015).

Akao et al., "A Purgative Action of Barbaloin Is Induced by *Eubacterium* sp. Strain BAR, a Human Intestinal Anaerobe, Capable of Transforming Barbaloin to Aloe-Emodin Anthrone," Biol. Pharm., 19(1):136-138 (1996).

Al-Eidan et al., "Clostridium difficile-associated diarrhoea in hospitalised patients," J. Clin. Pharm. Ther., 25(2):101-109 (2000).

Al-Nassir et al., "Comparison of Clinical and Microbiological Response to Treatment of Clostridium difficile-Associated Disease with Metronidazole and Vancomycin," Clin Infect Dis., 47(1):56-62 (2008).

Anand et al., "Epidemiology, clinical manifestations, and outcome of Clostridium difficile-associated diarrhea," Am J Gastroenterol., 89(4):519-23 (1994).

Ananthakrishnan et al., "Excess hospitalisation burden associated with Clostridium difficile in patients with inflammatory bowel disease," Gut, 57(2):205-210 (2007).

Anderson et al., "Systematic review: faecal microbiota transplantation in the management of inflammatory bowel disease," Aliment. Pharmacol. Ther., 36:503-16 (2012).

Andoh et al., "Terminal restriction fragment polymorphisum analyses of fecal microbiota in five siblings including two with ulcerative colitis," Journal of Clinical Gastroenterology, 2:343-345 (2009).

Andrews et al., "'Putting back the bugs': Bacterial Treatment Relieves Chronic Constipation and Symptoms of Irritable Bowel Syndrome," Med. J. Aust., 159(9):633-634 (1993).

Andrews et al., "Bacteriotherapy for Chronic Constipation—A Long Term Follow-Up," Gastroenterol, 108:A563 Abstract (1995).

Andrews et al., "Chronic Constipation (CC) may be reversed by Bacteriotherapy," Gastroenterol, 106:A459 (1994).

Andrews et al., "Chronic constipation reversed by restoration of bowel flora. A case and a hypothesis," European Journal of Gastroenterology & Hepatology, 4:245-247 (1992).

Anorexia nervosa, Encyclopedia Index A, healthAtoZ, Medical Network, Inc., pp. 1-7, n.d., Web, Nov. 23, 2005 <http://www.healthatoz.com/healthatoz/Atoz/ency/anorexia_nervosa.jsp>.

Arkkila et al., "Fecal Bacteriotherapy for Recurrent Clostridium difficile Infection," Gastroenterology, 138(5):S1-S5 (2010).

Aroniadis et al., "Intestinal Microbiota and the Efficacy of Fecal Microbiota Transplantation in Gastrointestinal Disease," Gastroenterology and Hepatology, 10(4): 230-7 (2014).

Aroniadis et al., "Long-Term Follow-up Study of Fecal Microbiota Transplantation (FMT) for Severe or Complicated Clostridium difficile Infection (CDI)," Gastroenterol, 144(Suppl 1):S185 (2013).

Atarashi et al., "Induction of Colonic Regulatory T Cells by Indigenous *Clostridium* Species," Science, 331(6015):337-341, published online Dec. 23, 2010.

Atarashi et al., "Treg induction by a rationally selected mixture of Clostridia strains from the human microbiota," Nature, 500(7461):232-236 (2013).

Atarashi et al., "WS/PP-064-03 Regulation of colonic regulatory T cells by *Clostridium* species," International Immunology, 22(Suppl 1, Part 3), pp. 1-3 (2010).

Atarashi et al., WS-064 Mucosal immunity: homeostasis, 14th ICIC Abstract book, 14th International Congress of Immunology, pp. iii131-iii133 (2010).

Autism, Health Encyclopedia—Diseases and Conditions, The Health Scout Network, pp. 1-5, n.d., Web, Nov. 22, 2005 <www.healthscout.com>.

Autism, Treatment, Prognosis, Healthcommunities.com, Inc., pp. 1-4, n.d., Web. Jan. 28, 2009 <http://www.neurologychannel.com/common/PrintPage.php>.

Autism: Mayo Clinic.com, Mayo Foundation for Medical Education and Research, pp. 1-7, May 31, 2008, Web. Jan. 28, 2009 <http://www.mayoclinic.com/print/autism/DS00348/METHOD=print&DSECTION=all>.

(56) References Cited

OTHER PUBLICATIONS

Backhed et al., "Host-bacterial mutualism in the human intestine," Science, 307(5717):1915-1920 (2005).
Backhed et al., "Mechanisms underlying the resistance to diet-induced obesity in germ-free mice," PNAS USA, 104(3):979-984 (2007).
Backhed et al., "The gut microbiota as an environmental factor that regulates fat storage," PNAS USA, 101(44):15718-15723 (2004).
Bakken et al., "Fecal bacteriotherapy for recurrent Clostridium difficile infection," Anaerobe, 15(6):285-289 (2009).
Bakken et al., "Treating Clostridium difficile Infection with Fecal Microbiota Transplantation," Clinical Gastroenterology and Hepatology, 9(12):1044-1049 (2011).
Bartlett et al., "Clinical recognition and diagnosis of Clostridium difficile infection," Clin Infect Dis., 46(Suppl 1):S12-S18 (2008).
Bartlett, "Clostridium difficile-associated Enteric Disease," Curr Infect Dis Rep., 4(6):477-483 (2002).
Belkaid et al., "Natural regulatory T cells in infectious disease," Nature Immunology, 6(4):353-360 (2005).
Bengmark et al., "Bioecological control of inflammatory bowel disease," Clinical Nutrition, 26(2):169-181 (2007).
Bennet et al., "Treatment of ulcerative colitis by implantation of normal colonic flora," Lancet, 333(8630):164 (1989).
Benson et al., "Changing epidemiology of Clostridium difficile-associated disease in children," Infect Control Hosp Epidemiol., 28(11):1233-1235 (2007).
Blaser et al., "What are the consequences of the disappearing human microbiota?" Nat. Microbiol., 7(12):887-894 (2009).
Blaser, "Who are we? Indigenous microbes and the ecology of human diseases," EMBO Rep, 7(10):956-960 (2006).
Bolte, "Autism and Clostridium tetani," Medical Hypotheses, 51(2):133-144 (1998).
Bolte, "Therapies for Gastrointestinal and Neurological Disorders," U.S. Appl. No. 60/214,813, filed Jun. 28, 2000.
Borody et al., "Anti-MAP Therapy for Pediatric Crohn's Disease," Am J Gastroenterol, 108(Suppl 1):S516 (2013).
Borody et al., "Anti-MAP Therapy in the Treatment of Active Crohn's Disease," J Gastroenterol & Hepatol, 20(Suppl):A2 (2005).
Borody et al., "Anti-MAP Rescues Anti-TNF Failures for Over 4 Years," Gastroenterol, 136(5)Suppl 1:A-681 (2009).
Borody et al., "Anti-mycobacterial therapy in Crohn's disease heals mucosa with longitudinal scars," Digestive & Liver Disease, 39(5):438-444 (2007).
Borody et al., "Anti-*Mycobacterium avium* SS Paratuberculosis (MAP) Therapy and Fistula Closure in Patients with Severe Crohn's Disease," Am J Gast, A101:S440 (2006).
Borody et al., "Bacteriotherapy in Chronic Fatigue Syndrome (CFS): A retrospective review," Am J Gastro, 107(S1):A1481 (2012).
Borody et al., "Bacteriotherapy Using Fecal Flora: toying with human motions" J. Clin. Gastroenterol., 38(6):475-483 (2004).
Borody et al., "Bowel-flora alteration: a potential cure for inflammatory bowel disease and irritable bowel syndrome?" Med. J. Aust., 150:604 (1989).
Borody et al., "Changes in Crohn's Disease Activity Index and C-Reactive Protein Levels During Anti-MAP Therapy," Am J Gastro, 104(S3):A1293 (2009).
Borody et al., "Clostridium difficile Complicating Inflammatory Bowel Disease: Pre- and Post- Treatment Findings," Gastroenterol, 134(4)Suppl 1:A-361 (2008).
Borody et al., "Could fecal microbiota transplantation cure all Clostridium difficile infections?," Future Microbiol, 9:1-3 (2014).
Borody et al., "Entamoeba histolytica: another cause of Crohn's Disease," AM J Gastro, 104(S3):A990 (2009).
Borody et al., "Faecal bacteriotherapy (FB) for chronic C. difficile (Cd) syndromes," J Gastroenterol Hepatol, 18(Suppl.):B8 (Abstract) (2003).
Borody et al., "Fecal bacteriotherapy in the treatment of recurrent C. difficile infection," UpToDate, pp. 1-6 (2006).
Borody et al., "Fecal Microbiota Transplantation (FMT) in Multiple Sclerosis (MS)," Am J Gastro, 106(S2):A942 (2011).
Borody et al., "Fecal microbiota transplantation and emerging applications," Nat. Rev. Gastroenterol. Hepatol., 9(2):88-96 (2011).
Borody et al., "Fecal microbiota transplantation for Clostridium difficile infection: A surgeon's perspective" Seminars in Colon and Rectal Surgery, 25:163-166 (2014).
Borody et al., "Fecal microbiota transplantation in gastrointestinal diseases—What practicing physicians should know," Polish Archives of Internal Medicine, 125(11):852-858 (2015).
Borody et al., "Fecal microbiota transplantation in the treatment of recurrent Clostridium difficile infection," UpToDate, pp. 1-4, (2015).
Borody et al., "Fecal Microbiota Transplantation in Ulcerative Colitis: Review of 24 Years Experience," Am J Gastro, 107(Supp 1):A1644 (2012).
Borody et al., "Fecal microbiota transplantation: a new standard treatment option for Clostridium difficile infection," Expert Rev Anti Infect Ther., 11(5):447-449 (2013).
Borody et al., "Fecal microbiota transplantation: current status and future directions," Expert Review of Gastroenterology & Hepatology, 5(6):653-655 (2011).
Borody et al., "Fecal Microbiota Transplantation. Expanding Horizons for Clostridium difficile Infections and Beyond," Antibiotics, 4:254-266 (2015).
Borody et al., "Fecal Microbiota Transplantation. Indications, Methods, Evidence, and Future Directions," Curr Gastroenterol Rep, 15:337-344 (2013).
Borody et al., "Fecal Microbiota Transplantation. Techniques, Applications, and Issues," Gastroenterol Clin North Am, 41:781-803 (2012).
Borody et al., "Irritable Bowel Syndrome and Dientamoeba Fragilis," ASM Sydney National Conference, pp. 4-5 (2002).
Borody et al., "Is Crohn's Disease Ready for Fecal Microbiota Transplantation?," J Clin Gastroenterol, 48(7):582-583 (2014).
Borody et al., "Myoclonus-dystonia affected by GI Microbiota?," AM J Gastro, 106(S2):A940 (2011).
Borody et al., "Novel appearance of healing mucosa following anti-*Mycobacterium avium* paratuberculosis therapy for Crohn's disease," J Gastroenterol Hepatol, 19(Suppl):A210 (2004).
Borody et al., Reversal of Idiopathic Thrombocytopenic Purpura [ITP] with Fecal Microbiota Transplantation [FMT], AM J Gastro, 106(S2):A941 (2011).
Borody et al., "Reversal of Inflammatory Bowel Disease (IBD) with Recurrent Faecal Microbiota Transplants (FMT)," AM J Gastro, 106(S2):A979 (2011).
Borody et al., "Severe recurrent Crohn's Disease of ileocolonic anastomosis and antimicrobial (anti-mycobacterial therapy)," Gut, 55:1211 (2006).
Borody et al., "The GI Microbiome and its Role in Chronic Fatigue Syndrome: a Summary of Bacteriotherapy," ACNEM Journal, 31(3):3-8 (2012).
Borody et al., "Therapeutic faecal microbiota transplantation: current status and future developments," Curr Opin Gastroenterol, 30:97-105 (2014).
Borody et al., "Treatment of chronic constipation and colitis using human probiotic infusions," Proceedings of Prebiotics and Probiotics and the New Foods Conference, 2-4:228 Abstract (2001).
Borody et al., "Treatment of First-time Clostridium difficile Infection with Fecal Microbiota Transplantation," Poster Presentation, 2015 ACG Annual Scientific Meeting, Honolulu, Hawaii, USA (2015).
Borody et al., "Treatment of Severe Constipation Improves Parkinson's Disease (PD) Symptoms," AM J Gastro, 104(S3):A999 (2009).
Borody et al., "Treatment of Severe Crohn's Disease (CD)—Using Rifabutin-Macrolide-Clofazimine Combination: Results at 30-37 Months," Gastroenterology, 118(4):A1334 Abstract (2000).
Borody et al., Treatment of Severe Crohn's Disease Using Rifabutin-Macrolide-Clofazimine Combination—Results at 38-43 Months, J Gastroenterol & Hepatol, 15(Suppl.):J102 (2000).
Borody et al., "Treatment of Severe Crohn's disease using antimycobacterial triple therapy—approaching a cure?," Digest Liver Dis, 34(1):29-38 (2002).

(56) References Cited

OTHER PUBLICATIONS

Borody et al., "Treatment of ulcerative colitis using fecal bacteriotherapy," J. Clin. Gastroenterol., 37(1):42-47 (2003).
Borody, "Bacteriotherapy for Chronic Fatigue Syndrome—A Long Term Follow-Up Study," Proceedings of ACMA Complementary Medicine Sydney, p. 1 (1995).
Borody, "Flora Power"—Fecal Bacteria Cure Chronic C. difficile Diarrhoea, Am J Gastroenterol, 95(11):3028-3029 (2000).
Borody, "Is the Infected Patient too 'Difficile' to Treat?," The Australian Society for Microbiology 2009 Perth, SY03 & SY03.1, p. 27 & 56, (2009).
Borody, "Letter to the Editor—Response to Drs. Famularo et al.," AJG, 96(7):2262-2264 (2001).
Bowden et al., "Pseudomembraneous enterocolitis: mechanism of restoring floral homeostasis," Am Surg., 47(4):178-183 (1981).
Borriello, "Clostridial Disease of the Gut," Clinical Infectious Diseases, The University of Chicago, 20(Suppl 2):S242-S250 (1995).
Brandt et al., "Endoscopic Fecal Microbiota Transplantation: "First-Line" Treatment for Severe Clostridium difficile Infection?" J. Clin. Gastroenterol., 45(8):655-657 (2011).
Brandt et al., "Fecal microbiota transplantation for recurrent Clostridium difficile infection," Clin Gastroenterol., 45(Suppl):S159-S167 (2011).
Brandt et al., "Long-Term Follow-Up Study of Fecal Microbiota Transplantation (FMT) for Ulcerative Colitis (UC)," Am. J. Gastroenterol., 107(Suppl 1):S657 (2012).
Brandt et al., Safety of Fecal Microbiota Transplantation (FMT) in Immunocompromised (Ic) Patients with Inflammatory Bowel Disease (IBD), Am J Gastroenterol, 108(Suppl 1):S556 (2013).
Browne et al., "Culturing of 'unculturable' human microbiota reveals novel taxa and extensive sporulation," Nature, 533(7604):543-546 (2016).
Bueche et al., "Quantification of Endospore-Forming Firmicutes by Quantitative PCR with the Functional Gene spo0A," Applied and Environmental Microbiology, 79(17):5302-5312 (2013).
Cammorata et al., "Review article: biofile formation by Helicobacter pylori as a target for eradication of resistant infection," Aliment Pharmacol Ther, 36:222-30 (2012).
Campbell et al., "The many faces of Crohn's Disease: Latest concepts in etiology," OJIM, 2(2):107-115 (2012).
Cano et al., "Revival and identification of bacterial spores in 25-40 million year old Dominican Amber Science," Science, 268(5213):1060-1064 (1995).
Cato et al., "Clostridium oroticum comb. nov. amended description," International Journal of Systematic Bacteriology, 17(1):9-13 (1968).
Celik et al., "Factors influencing the stability of freeze-dried stress-resilient and stress-sensitive strains of bifidobacteria," J. Dairy Sci., 96(6):3506-16 (2013).
Center for Disease Control, "Severe Clostridium difficile-associated disease in populations previously at low risk—four states, 2005." Morbidity and Mortality Weekly Report, 54(47):1201-1205 (2005).
Chamberlain et al., "MAP-associated Crohn's Disease, MAP, Koch's postulates, causality and Crohn's Disease," Digestive and Liver Disease, 39:790-794 (2007).
Chamberlin et al., "Primary treatment of Crohn's disease: combined antibiotics taking center stage," Expert Rev. Clin. Immunol., 7(6):751-760 (2011).
Chang et al., "Decreased diversity of the fecal Microbiome in recurrent Clostridium difficile-associated diarrhea," J. Infect. Dis., 197(3):435-438 (2008).
Chen et al., "A mouse model of Clostridium difficile-associated disease," Gastroenterology, 135(6):1984-1992 (2008).
Cherif et al., "Thuricin 7: a novel bacteriocin produced by Bacillus thuringiensis BMG1.7, a new strain isolated from soil," Letters in Applied Microbiology, 32:243-7 (2001).
Choi et al., "Fecal Microbiota Transplantation: Current Applications, Effectiveness, and Future Perspectives," Clin. Endosc., 49:257-265 (2016).

Chopra et al., "Recent epidemiology of Clostridium difficile infection during hematopoietic stem cell transplantation," Clin Transplant., 25(1):E82-E87 (2011).
Chu et al., "Profiling Living Bacteria Informs Preparation of Fecal Microbiota Transplantations," PLOS One, 1-16 (2017).
Citron et al., "In Vitro Activities of CB-183,315, Vancomycin, and Metronidazole against 556 Strains of Clostridium difficile, 445 Other Intestinal Anaerobes, and 56 Enterobacteriaceae Species," Antimicrob Agents Chemother., 56(3):1613-1615 (2012).
Claesson et al., "Comparison of two next-generation sequencing technologies for resolving highly complex microbiota composition using tandem variable 16S rRNA gene regions," Nucleic Acids Research, 38(22):1-13 (2010).
Clancy et al., "Anti-MAP Therapy Induces and Maintains Remission in Severe Crohn's Disease," Ann NY Acad Sci, p. 1 (2005).
Claus et al., "Colonization-induced host-gut microbial metabolic interaction," MBio, 2(2):e00271-00210 (2011).
Claus et al., "Systemic multicompartmental effects of the gut microbiome on mouse metabolic phenotypes," Mol. Syst. Biol., 4(1):219 (2008).
Cohen et al., "Clinical practice guidelines for Clostridium difficile infection in adults: 2010 update by the society for healthcare epidemiology of America (SHEA) and the infectious diseases society of America (IDSA)," Infect Control Hosp Epidemiol., 31(5):431-55 (2010).
Collins et al., "The Phylogeny of the Genus *Clostridium*: Proposal of Five New Genera and Eleven New Species Combinations," International Journal of Systematic Bacteriology, pp. 812-826 (1994).
Crowther, "Transport and Storage of Faeces for Bacteriological Examination," Journal of Applied Bacteriology, 34(2):477-483 (1971).
Cutolo et al., "Fecal feedings as a therapy in *Staphylococcus enterocolitis*," NY State J Med, 59:3831-3833 (1959).
Dale et al., "Molecular interactions between bacterial symbionts and their hosts," Cell, 126(3):453-465 (2006).
Dan et al., "Comparison of preservation media and freezing conditions for storage of specimens of faeces," J. Med Microbiology, 28:151-154 (1989).
De Giulio et al., "Use of Algiinate and Cryo-Protective Sugars to Improve the Viability of Lactic Acid Bacteria After Freezing and Freeze-Drying," World Journal of Microbiology & Biotechnology, 21:739-746 (2005).
Defang et al., "In vitro and in vivo evaluation of two extended release preparations of combination metformin and glipizide," Drug Develop. & Indust. Pharm., 31:677-685 (2005).
Dendukuri et al., "Probiotic therapy for the prevention and treatment of Clostridium difficile-associated diarrhea: a systematic review," CMAJ, 173(2):167-170 (2005).
Derwent Abstract Accession No. 98-230427/20, WO 98/13068 A, (Kuperman VB) Apr. 2, 1998.
Dethlefsen et al., "An ecological and evolutionary perspective on human-microbe mutualism and disease," Nature, 449(7164):811-818 (2007).
Dewhirst et al., "Phylogeny of the Defind Murine Microbiota: Altered Schaedler Flora," Applied and Environmental Microbiology, 65(8):3287-3292 (1999).
DuPont, "The search for effective treatment of Clostridium difficile infection," N Engl J Med., 364(5):473-475 (2011).
Eckburg et al., "Diversity of the human intestinal microbial flora," Science, 308(5728):1635-1638 (2005).
Eiseman et al., "Fecal enema as an adjunct in the treatment of pseudomembranous enterocolitis," Surgery, 44(5):854-859 (1958).
Extended European Search Report dated Apr. 3, 2014, in European Patent Application No. 11813951.8.
Extended European Search Report dated Nov. 30, 2016, in European Patent Application No. 16193790.9.
Faust et al., "Treatment of recurrent pseudomembranous colitis (RPMC) with stool transplantation (ST): Report of six (6) cases," Can J Gastroenterol., 16:A43 (2002).
Fenton et al., "Pseudomembranous colitis associated with antibiotic therapy—an emerging entity," Can Med Assoc J., 111(10):1110-1111 (1974).

(56) References Cited

OTHER PUBLICATIONS

Floch et al., "Probiotics and Dietary Fiber, The Clinical Coming of Age of Intestinal Microecology," J. Clin. Gastroenterology, 27(2):99-100 (1998).
Floch, "Fecal Bacteriotherapy, Fecal Transplant, and the Microbiome," J. Clin. Gastroenterol., 44(8):529-530 (2010).
Flotterod et al., "Refractory Clostridium difficile infection. Untraditional treatment of antibiotic-induced colitis," Tidsskr Nor Laegeforen, 111:1364-1365 (1991).
Frank et al., "Molecular-phylogenetic characterization of microbial community imbalances in human inflammatory bowel diseases," PNAS, 104(34):13780-13785 (2007).
Frantzen et al., "Empirical evaluation of preservation methods for faecal DNA," Molecular Ecology, 7(10):1423-1428 (1998).
Freeman et al "The changing epidemiology of Clostridium difficile infections," Clin Microbiol. Rev., 23(3):529-549 (2010).
Frese et al., "The evolution of host specialization in the vertebrate gut symbiont Lactobacillus reuteri," PloS Genet., 7(2):e1001314 (2011).
Gaboriau-Routhiau et al., "The Key Role of Segmented Filamentous Bacteria in the Coordinated Maturation of Gut Helper T Cell Responses," Immunity, 31(4):677-689 (2009).
Garborg et al., "Results of faecal donor instillation therapy for recurrent Clostridium difficile-associated diarrhoea," Scand J Infect Dis., 42(11-12):857-61 (2010).
Garey et al., "Meta-analysis to assess risk factors for recurrent Clostridium difficile infection," J. Hosp. Infect., 70(4):298-304 (2008).
Gerding, "Management of Clostridium difficile infection. thinking inside and outside the box," Clin Infect Dis., 51(11):1306-13 (2010).
Geuking et al., "Intestinal Bacterial Colonization Induces Mutualistic Regulatory T Cell Respones," Immunity, 34:794-806 (2011).
Gitlin et al., "*Mycobacterium avium* ss paratuberculosis-associated Diseases: Piecing the Crohn's Puzzle Together," J Clin Gastroenterol, 46(8):649-655 (2012).
Gough et al., "Systematic review of intestinal microbiota transplantation (fecal bacteriotherapy) for recurrent Clostridium difficile infection," Clin. Infect. Dis., 53(10):994-1002 (2011).
Grehan et al., "Durable alteration of the colonic microbiota by the administration of donor fecal flora," Journal of Clinical Gastroenterology, 44(8):551-561 (2010).
Guarner et al., "Gut flora in health and disease," Lancet, 361(9356):512-519 (2003).
Gustafsson et al., "The Effect of Faecal Enema on Five Microflora-Associated Characteristics in Patients with Antibiotic-Associated Diarrhoea," Scandinavian Journal of Gastroenterology, 34:580-586 (1999).
Gustafsson et al., "Faecal Short-Chain Fatty Acids in Patients with Antibiotic-Associated Diarrhoea, before and after Faecal Enema Treatment" Scand J Gastroenterol, 33:721-727 (1998).
Hamilton et al., "Change in microbial community composition of in patients with recalcitrant Clostridium difficile colitis treated with fecal bacteriotherapy," International Human Microbiome Congress, Poster and Presentation, Vancouver, ON, Canada, Mar. 9-11, 2011.
Hamilton et al., "High-throughput DNA sequence analysis reveals stable engraftment of gut microbiota following transplantation of gut microbiota following transplantation of previously frozen fecal bacteria," Gut Microbes, 4(2):1-11 (2013).
Hamilton et al., "Standardized Frozen Preparation for Transplantation of Fecal Microbiota for Recurrent Clostridium difficile Infection," Article and Supplementary Material, Am. J. Gastroenterol., 107(5):761-767 (2012).
Hayashi et al., "Phylogenetic Analysis of the Human Gut Microbiota Using 16S rDNA Clone Libraries and Strictly Anaerobic Culture-Based Methods," Microbiol. Immunol., 46(8):535-548 (2002).
Hecker et al., "Fecal Microbiota Transplantation by Freeze-Dried Oral Capsules for Recurrent Clostridium difficile Infection," Open Forum Infect Dis, 3(2): 1-2 (2016).
Hellemans et al., "Fecal transplantation for recurrent Clostridium difficile colitis, an underused treatment modality," Acta Gastroenterol Belg., 72(2):269-70 (2009).
Henriksson et al., "Probiotics under the regulatory microscope," Expert Opin. Drug Saf., 4(6):1-9 (2005).
Hensel et al., "Vagal Ascent and Distribution of 125 I-Tetanus Toxin after Injection into the Anterior Wall of the Stomach," Naunyn-Schmiedeberg's Arch. Pharmacol, 276:395-402 (1973).
Honda et al., "Regulation of T Cell Responses by Intestinal Commensal Bacteria," Journal of Intestinal Microbiology, vol. 25, 2nd Edition:104 (2011).
Hooper et al., "How host-microbial interactions shape the nutrient environment of the mammalian intestine," Annu. Rev. Nutr., 22:283-307 (2002).
Hope et al., "Sporadic colorectal cancer-role of the commensal microbiota," FEMS Microbiol. Lett., 244:1-7 (2005).
Hota et al., "Determining Mortality Rates Attributable to Clostridium difficile Infection," Emerg. Infect. Dis., 18(2):305-307 (2012).
Hota et al., "Oral Vancomycin Followed by Fecal Transplant Versus Tapering Oral Vancomycin," U.S. National Institutes of Health, Clinical Study No. NCT01226992, Oct. 20, 2010, last updated Jan. 14, 2013, Web, May 20, 2014, pp. 1-4 <http://clinicaltrials.gov/ct2/show/NCT01226992>.
Hu et al., "Prospective derivation and validation of a clinical prediction rule for recurrent Clostridium difficile infection," Gastroenterology, 136:1206-1214 (2009).
Huang et al., "Once-daily propranolol extended-release tablet dosage form: formulation design and in vitro/in vivo investigation," European J. of Pharm. & Biopharm., 58:607-614 (2004).
Huttenhower et al., "Structure, function and diversity of the healthy human microbiome," The Human Microbiome Project Consortium, Nature, 486:207-214 (2012).
Immunology in the 21st Century: Defeating Infection, Autoimmunity, Allergy, and Cancer, ICI 2010 Wrap-up Report, 14th International Congress of Immunology, pp. 1 (2010).
Inflammatory Bowel Disease Facts, Disease Prevention and Treatment Strategies, Crohn's Disease and Inflammatory Bowel Disease (IBD), HealingWithNutrition.com, pp. 1-4, n.d., Web, Oct. 23, 2005 <http://www.HealingWithNutrition.com/disease/inflambowels/chrohns.html>.
International Preliminary Examination Report completed Nov. 19, 2002, in International Application No. PCT/AU2001/000907, 19 pgs.
International Preliminary Report on Patentability completed Dec. 12, 2012, in International No. PCT/AU2011/000987, 35 pgs.
International Preliminary Report on Patentability completed Mar. 12, 2015, in International Application No. PCT/AU2013/001362, 29 pgs.
International Preliminary Report on Patentability dated Sep. 10, 2013, in International Application No. PCT/US2012/028484, 10 pgs.
International Search Report and Written Opinion dated Aug. 8, 2016, in International Application No. PCT/US2016/032695, 10 pgs.
International Search Report and Written Opinion dated Feb. 5, 2014, in International Application No. PCT/AU2013/001362, 17 pgs.
International Search Report and Written Opinion dated Jul. 31, 2014, in International Application No. PCT/US2014/027391, 16 pgs.
International Search Report and Written Opinion dated Oct. 28, 2011, in International No. PCT/AU2011/000987, 18 pgs.
International Search Report dated Aug. 10, 2012, in International Application No. PCT/US2012/028484, 7 pgs.
International Search Report dated Jul. 29, 2014, in International Application No. PCT/AU2014/000478, 7 pgs.
International Search Report dated Sep. 22, 2017, in International Application No. PCT/US2017/040591, 12 pgs.
Irrgang et al., "The historical Development of Mutaflor therapy," Ardeypharm GmbH, pp. 1-38 (1988) <http://www.ardeypharm.de/pdfs/en/mutaflor_historical_e.pdf?>.
Irritable Bowel Syndrome (IBS), Health A to Z, InteliHealth, pp. 1-4, n.d., Web, Oct. 23, 2005 <http://www.intelihealth.com>.

(56) References Cited

OTHER PUBLICATIONS

Issa et al., "Clostridium difficile and Inflammatory Bowel Disease," Inflamm Bowel Dis., 14(10):1432-1442 (2008).
Issa et al., "Impact of Clostridium difficile on inflammatory bowel disease," Clin. Gastroenterol. Hepatol., 5(3):345-351 (2007).
Itoh et al., "Characterization of clostridia isolated from faeces of limited flora mice and their effect on caecal size when associated with germ-free mice," Laboratory Animals, 19:111-118 (1985).
Itoh et al., "Intestinal bacteria antagonistic to Clostridium difficile in mice," Laboratory Animals, 21:20-25 (1987).
Ivanov et al., "Specific Microbiota Direct the Differentiation of IL-17-Producing T-Helper Cells in the Mucosa of the Small Intestine," Cell Host & Microbe, 4:337-349 (2008).
Jacob et al., "Single Delivery of High-Diversity Fecal Microbiota Preparation by Colonoscopy Is Safe and Effective in Increasing Microbial Diversity in Active Ulcerative Colitis," Inflamm Bowel Dis., 0(0):1-9 (2017).
Janeway et al., "Adaptive Immunity to Infection," Immunobiology, 6th Edition, Chapter 10, pp. 414 (2005).
Janeway, Jr. et al., "Autoimmune responses are directed against self antigens," Immunobiology: The Immune System in Health and Disease, 5th Edition, pp. 1-4 (2001).
Jarvis et al., "National point prevalence of Clostridium difficile in US health care facility inpatients, 2008," Am. J. Infect. Control, 37:263-270 (2009).
Johnson et al., "Interruption of Recurrent Clostridium difficile-Associated Diarrhea Episodes by Serial Therapy with Vancomycin and Rifaximin," Clin. Infect. Dis., 44(6):846-848 (2007).
Johnson et al., "Rifaximin Redux: Treatment of recurrent Clostridium difficile infections with Rifaximin immediately post-vancomycin treatment," Anaerobe, 15(6):290-291 (2009).
Kageyama et al., "Emendation of genus *Collinsella* and proposal of *Collinsella stercorin* sp. nov. and *Collinsella intestinalis* sp. nov.," International Journal of Systematic and Evolutionary Microbiology, 50:1767-1774 (2000).
Kageyama et al., "Phylogenetic and phenotypic evidence for the transfer of Eubacterium aerofaciens to the genus *Collinsella* as *Collinsella aerofaciens* gen. nov., comb. nov.," International Journal of Systematic Bacteriology, 49:557-565 (1999).
Kakihana et al., "Fecal microbiota transplantation for patients with steriod-resistant acute graft-versus-host disease of the gut," Blood, 128(16):2083-2088 (2016).
Kamboj et al., "Relapse versus reinfection: surveillance of Clostridium difficile infection," Clin Infect Dis., 53(10):1003-1006 (2011).
Kang et al., "Microbiota Transfer Therapy alters gut ecosystem and improves gastrointestinal and autism symptoms: an open-label study," Microbiome, 5:10, 16 pages (2017).
Karas et al., "A review of mortality due to Clostridium difficile infection," J Infect., 61(1):1-8 (2010).
Kassam et al., "Fecal transplant via retention enema for refractory or recurrent Clostridium difficile infection," Arch Intern Med., 172(2):191-193 (2012).
Kelly et al., "Commensal gut bacteria: mechanisms of immune modulation," TRENDS in Immunology, 26(6):326-333 (2005).
Kelly et al., "Clostridium difficile—more difficult than ever," N. Engl. J. Med., 359(18):1932-1940 (2008).
Kelly et al., "Clostridium difficile colitis," N. Engl. J. Med., 330(4):257-62 (1994).
Kelly et al., "Fecal Microbiota Transplant for Treatment of Clostridium difficile Infection in Immunocompromised Patients," Am J Gastroenterol, 109:1065-1071 (2014).
Kelly et al., "Fecal microbiota transplantation for relapsing Clostridium difficile infection in 26 patients: methodology and results," J. Clin. Gastroenterol., 46(2):145-149 (2012).
Keynan et al., "The Role of Regulatory T Cells in Chronic and Acute Viral Infections," Clinical Infectious Diseases, 46:1046-1052 (2008).
Khanna et al., "A Novel Microbiome Therapeutic Increases Gut Microbial Diversity and Prevents Recurrent Clostridium difficile Infection," The Journal of Infectious Diseases, 214:173-81 (2016).
Khanna et al., "The epidemiology of community-acquired Clostridium difficile infection: a population-based study," Am J Gastroenterol., 107(1):89-95 (2012).
Khanna et al., "The growing incidence and severity of Clostridium difficile infection in inpatient and outpatient settings," Expert Rev Gastroenterol Hepatol., 4(4):409-16 (2010).
Kharidia et al., "The Activity of a Small Lytic Peptide PTP-7 on *Staphylococcus aureus* Biofilms," J. Microbiol., 49(4):663-668 (2011).
Khoruts et al., "Changes in the composition of the human fecal microbiome after bacteriotherapy for recurrent Clostridium difficile-associated diarrhea," J. Clin. Gastroenterol., 44(5):354-360 (2010).
Khoruts et al., "Therapeutic transplantation of the distal gut microbiota," Mucosal Immunol., 4(1):4-7 (2011).
Kim et al., "Effect of Rifampin on the Plasma Concentration and the Clinical Effect of Haloperidol Concomitantly Administered to Schizophrenic Patients," Journal of Clinical Psychopharmacology, 16(3):247-252 (1996).
Kim et al., "In Vitro Culture Conditions for Maintaining a Complex Population of Human Gastrointestinal Tract Microbiota," Journal of Biomedicine and Biotechnology, 2011(Article ID 838040):1-10 (2011) <http://www.hindawi.com/journals/bmri/2011/838040/>.
Klaenhammer, "Bacteriocins of lactic acid bacteria," Biochimie, 70:337-49 (1988).
Kleiman et al., "Comparison of two coprological methods for the veterinary diagnosis of fasciolosis," Arquivo Brasileiro de Medicina Veterinária e Zootécnica, 55(2):181-185 (2005).
Kobashi et al., "Metabolism of Sennosides by Human Intestinal Bacteria," Journal of Medicinal Plant Research, 40(3):225-236 (1980).
Koch, "What size should a bacterium be? A question of scale," Annu. Rev. Microbiol., 50:317-48 (1996).
Krogius-Kurikka et al., "Sequence analysis of percent G+C fraction libraries of human faecal bacterial DNA reveals a high number of Antinobacteria," BMC Microbiology, 9(68):1-13 (2009).
Kuijper et al., "Update of Clostridium difficile Infection due to PCR Ribotype 027 in Europe, 2008," Euro. Surveill., 13(31):Article 5 (2008).
Kuksal et al., "Formulation and In Vitro, In Vivo Evaluation of Extended-release Matrix Tablet of Zidovudine: Influence of Combination of Hydrophilic and Hydrophobic Matrix Formers," AAPS Pharm., 7(1):E1-E9 (2006).
Kunde et al., "Safety, Tolerability, and Clinical Response After Fecal Transplantation in Children and Young Adults With Ulcerative Colitis," JPNG, 56(6):597-601 (2013).
Kyne et al., "Associated between antibody response to toxin A and protection against recurrent Clostridium difficile diarrhea," Lancet, 357(9251):189-93 (2001).
Kyne et al., "Asymptomatic carriage of Clostridium difficile and serum levels of IgG antibody against toxin A," N Engl J Med., 342(6):390-397 (2000).
Kyne et al., "Factors associated with prolonged symptoms and severe disease due to Clostridium difficile," Age and Ageing, 28(2):107-13 (1999).
Kysela et al., "Serial analysis of V6 ribosomal sequence tags (SARST-V6): a method for efficient, high-throughput analysis of microbial community composition," Environmental Microbiology, 7(3):356-364 (2005).
Labbé et al., "Clostridium difficile infections in a Canadian tertiary care hospital before and during a regional epidemic associated with the BI/NAP1/027 strain," Antimicrob Agents Chemother., 52(9):3180-7 (2008).
Lamontagne et al., "Impact of emergency colectomy on survival of patients with fulminant Costridium difficile colitis during an epidemic caused by a hypervirulent strain," Ann. Surg., 245(2):267-272 (2007).
Larsen et al., "Gut Microbiota in Human Adults with Type 2 Diabetes Differs from Non-Diabetic Adults," PLoS ONE, 5(2): e9085-e9095 (2010).
Lau et al., "Bacteraemia caused by Anaerotruncus colihominisand emended desciption of the species," J Clin Pathol, 59:748-752 (2006).

(56) References Cited

OTHER PUBLICATIONS

Lawson et al., "*Anaerotruncus colihominis* gen. nov., sp. nov., from human faeces," International Journal of Systematic and Evoluntionary Microbiology, 54:413-417 (2004).
Lawson et al., "Anaerotruncus," Bergey's Manual of Systematics of Archae and Bacteria, pp. 1-4 (2009).
Lee, "A Prospective Randomized Multi-Centre Trial of Fresh vs. Frozen-and-Thawed Human Biotherapy (Fecal Transplant) for Recurrent Clostridium difficile Infection," U.S. National Institutes of Health, Clinical Study No. NCT01398969, pp. 1-4, last updated Feb. 27, 2014, Web, May 20, 2014 <http://clinicaltrials.gov/ct2/show/NCT01398969>.
Leis et al., "Fecal microbiota transplantation: A 'How-To' guide for nurses," Collegian, 22:445-451 (2015).
Lewis et al., "Stool form scale as a useful guide to intestinal transit time," Scand. J. Gastroenterol., 32(9):920-924 (1997).
Ley et al., "Ecological and evolutionary forces shaping microbial diversity in the human intestine," Cell, 124:837-848 (2006).
Ley et al., "Evolution of mammals and their gut microbes," Science, 320(5883):1647-1651 (2008).
Ley et al., "Microbial ecology. human gut microbes associated with obesity," Nature, 444(7122):1022-3 (2006).
Ley et al., "Worlds within worlds: evolution of the vertebrate gut microbiota," Nat. Rev. Microbiol., 6(10):776-788 (2008).
Lin et al., "Twelve Week Storage Trial of Microbial Viability in Lyophilized and Frozen Fecal Microbiota Preparations," Poster Presentation—Digestive Disease Week 2015, Washington, D.C. USA.
Longstreth, "Irritable bowel syndrome: A multibillion-dollar problem," Gastroenterology, 109(6):2029-2031 (1995).
Loo et al., "A predominantly clonal multiinstitutional outbreak of Clostridium difficile-associated diarrhea with high morbidity and mortality," N Engl J Med, 353(23):2442-9 (2005).
Loo et al., "Host and pathogen factors for Clostridium difficile infection and colonization," N Engl J Med, 365(18):1693-703 (2011).
Louie et al., "Fidaxomicin versus vancomycin for Clostridium difficile infection," N. Engl. J. Med., 364(5):422-431 (2011).
Louie et al "Home-based fecal flora infusion to arrest multiply-recurrent C. difficile infection," ICAAC/IDSA Conference, Abstract #K-4201 (2008).
Louis et al., "Diversity, metabolism and microbial ecology of butyrate-producing bacteria from the human large intestine," FEMS Microbiology Letters, 294:1-8 (2009).
Lu, "Taboo transplant: How new poo defeats superbugs," Science News, 1:90-91 (2011).
Ludwig et al., "Taxonomic outline of the phylum Firmicutes," Bergey's Manual of Systematic Bacteriology, 3:15-17 (2009).
Lund-Tonnesen et al., "Clostridium difficile-associated diarrhea treated with homologous faeces," Tidsskr Nor Lageforen, 118:1027-1030 (1998).
MacConnachie et al., "Faecal transplant for recurrent Clostridium difficile-associated diarrhoea: a UK case series," QJM, 102(11):781-784 (2009).
MacDonald et al., "Formation of Ursodeoxycholic Acid from Chenodeoxycholic Acid by a 7β-Hydroxysteroid Dehydrogenase-Elaborating Eubacterium aerofaciens Strain Cocultured with 7α-Hydroxysteroid Dehydrogenase-Elaborating Organisms," Applied and Environmental Microbiology, 44(5):1187-1195 (1982).
Macpherson et al., "Induction of Protective IgA by Intestinal Dendritic Cells Carrying Commensal Bacteria," Science, 303:1662-1665 (2004).
Madsen, "The use of probiotics in gastrointestinal disease," Can J Gastroenterol, 15(12):817-22 (2001).
Maizels et al., "Regulatory T cells in Infection," Advances in Immunology, Chapter 3, 112:73-136 (2011).
Marchesi et al., "The normal intestinal microbiota," Curr. Opin. Infect. Dis., 20(5):508-513 (2007).
Martin, "Development and Delivery of a Treatment for Clostridium difficile," Bacteriotherapy, pp. 1-2, n.d., Web, Feb. 10, 2012 <www.bacteriotherapy.org>.
Martin-Dejardin et al., "A way to follow the viability of encapsulated Bifidobacterium bifidum subjected to a freeze-drying process in order to target the colon: Interest of flow cytometry," European Journal of Pharmaceutical Sciences, 49:166-74 (2013).
Maslowski et al., "Diet, gut microbiota and immune responses," Nat Immunol., 12(1):5-9 (2011).
McDonald et al., "An Epidemic, Toxin Gene-Variant Strain of Clostridium difficile," N Engl J Med., 353(23):2433-41 (2005).
McDonald et al., "Clostridium difficile Infection in Patients Discharged from US Short-stay Hospitals, 1996-2003" Emerg. Infect. Dis, 12(3):409-415 (2006).
McFarland et al., "Breaking the Cycle: Treatment Strategies for 163 Cases of Recurrent Clostridium difficile Disease," Am. J. Gastroenterol., 97(7):1769-1775 (2002).
McFarland et al., "Implications of the changing face of Clostridium difficile disease for health care practitioners," Am J Infect Control., 35(4):237-253 (2007).
McFarland et al., "Meta-Analysis of Probiotics for the Prevention of Antibiotic Associated Diarrhea and the Treatment of Clostridium difficile Disease," Am J Gastroenterol., 101(4):812-22 (2006).
McFarland et al., "Nosocomial Acquisition of Clostridium Difficile Infection," N Engl J Med., 320(4):204-210 (1989).
McFarland et al., "Recurrent Clostridium Difficile Disease: Epidemiology and Clinical Characteristics," Infect Control Hosp Epidemiol., 20(1):43-50 (1999).
McFarland et al., "Renewed interest in a difficult disease: Clostridium difficile infections—epidemiology and current treatment strategies," Curr Opin Gastroenterol., 25(1):24-35 (2008).
Miller et al., "Health care-associated Clostridium difficile infection in Canada: patient age and infecting strain type are highly predictive of severe outcome and mortality," Clin Infect Dis., 50(2):194-201 (2010).
Miller et al., "Long-term follow-up of patients with fulminant Clostridium difficile colitis," J. Gastrointest. Surg., 13(5):956-959 (2009).
Miller et al., "Morbidity, mortality, and healthcare burden of nosocomial Clostridium difficile-associated diarrhea in Canadian hospitals," Infect Control Hosp Epidemiol., 23(3):137-40 (2002).
Miller, "The fascination with probiotics for Clostridium difficile infection: lack of evidence for prophylactic or therapeutic efficacy," Anaerobe, 15(6):281-284 (2009).
Moayyedi et al., "Fecal Microbiota Transplantation Induces Remission in Patients With Active Ulcerative Colitis in a Randomized Controlled Trial," Gastroenterology, 149(1):102-9 (2015).
Molecular Studies in Autism, 2004 Funding Cycle, Cure Autism Now, Cure Autism Now Foundation, pp. 1-7 (2005) <www.cureautismnow.org>.
Momose et al., "16S rRNA gene sequence-based analysis of clostridia related to conversion of germfree mice to the normal state," Journal of Applied Microbiology, 107:2088-2097 (2009).
Morris et al., "Clostridium difficile Colitis: An Increasingly Aggressive Iatrogenic Disease?" Arch Surg., 137(10):1096-1100 (2002).
Mullard, "Microbiology: The Inside Story," Nature, 453:578-580 (2008).
Mutaflor, "Brief Summary of Therapeutic Principles," Ardeypharm GmbH 0796 D-58313 Herdecke Germany, 6 pgs (2006).
Mutaflor, "For Functional and Inflammatory Bowel Diseases for Extraintestinal Manifestations for Activation of the Body's In-Built Defences," Ardeypharm GmbH 0796, D-58313 Herdecke Germany, 8 pgs (2006).
Mutaflor, "Safety of Therapy," Ardeypharm GmbH 0796, D-58313 Herdecke Germany, 4 pgs (1988).
Muto et al., "A Large Outbreak of Clostridium difficile-Associated Disease with an Unexpected Proportion of Deaths and Colectomies at a Teaching Hospital Following Increased Fluoroquinolone Use," Infect Control Hosp Epidemiol., 26(3):273-80 (2005).
Nieuwdorp et al., ["Treatment of recurrent Clostridium difficile-associated diarrhoea with a suspension of donor faeces"], Ned Tijdschr Geneeskd, 152(35):1927-32 (2008) (English absract).

(56) References Cited

OTHER PUBLICATIONS

Niu et al., "Prevalence and Impact of Bacteriophages on the Presence of Escherichia coli O157:H7 in Feedlot Cattle and Their Environment," Applied and Environmental Microbiology, 75(5): 1271-8 (2009).
O'Hara et al., "The gut flora as a forgotten organ," EMBO Rep., 7(7):688-693 (2006).
O'Brien et al., "The emerging infectious challenge of clostridium difficile-associated disease in Massachusetts hospitals: clinical and economic consequences," Infect Control Hosp Epidemiol., 28(11):1219-27 (2007).
O'Connor et al., "Clostridium difficile Infection Caused by the Epidemic BI/NAP1/027 Strain," Gastroenterology, 136(6):1913-1924 (2009).
Office Action dated Sep. 18, 2015, in European Patent Application No. 11 728 077.6.
O'Garra et al., "IL-10--producing and naturally occuring CD4+ Tregs: limiting collateral damage," The Journal of Clinical Investigation, 114:1372-1378 (2004).
Okada et al., "Effects of Fecal Microorganisms and Their Chloroform-Resistant Variants Derived from Mice, Rats, and Humans on Immunological and Physiological Characteristics of the Intestines of Ex-germfree Mice," Infection and Immunity, 62(12):5442-5446 (1994).
Ott et al., "Efficacy of Sterile Fecal Filtrate Transfer for Treating Patients With Clostridium difficile Infection," Gastroenterology, 152(4):799-811 (2017).
Paramsothy et al., "Gastroenterologist perceptions of faecal microbiota transplantation," World J Gastroenterol, 21(38): 10907-10914 (2015).
Paramsothy et al., "Multidonor intensive faecal microbiota transplantation for active ulcerative colitis: a randomised placebo-controlled trial," The Lancet, published online, 11 pages (2017).
Patterson et al., "Special organism isolation: attempting to bridge the gap," Infect Control Hosp Epidemiol., 15(5):335-338 (1994).
Pearce et al., "Modification of the colonic microflora using probiotics: The way forward?," Gut, 41(Suppl 3):A63 (1997).
Pearce et al., "The use of probiotic therapy as a novel approach to the management of irritable bowel syndrome: a preliminary study," J Gastroenterol & Hepatol, 12(Suppl):A129 (1997).
Pépin et al., "Clostridium difficile-associated diarrhea in a region of Quebec from 1991 to 2003: a changing pattern of disease severity," CMAJ, 171(5):466-472 (2004).
Pépin et al., "Emergence of Fluoroquinolones as the Predominant Risk Factor for Clostridium difficile-Associated Diarrhea: A Cohort Study During an Epidemic in Quebec," Clin Infect Dis., 41(9):1254-1260 (2005).
Pépin et al., "Management and Outcomes of a First Recurrence of Clostridium difficile-Associated Disease in Quebec, Canada," Clin. Infect. Dis., 42:758-764 (2006).
Persky et al., "Treatment of recurrent Clostridium difficile-associated diarrhea by administration of donated stool directly through a colonoscope," Am J Gastroenterol., 95(11):3283-3285 (2000).
Petrof et al., "Stool substitute transplant therapy for the eradication of Clostridium difficile infection: 'RePOOPulating' the gut," Microbiome, 1:3 (2013).
Petrof, "Harnessing the healthy gut microbiota to cure patients with recurrent C. difficile infection," U.S. National Institutes of Health, Clinical Study No. NCT01372943, pp. 1-2, last updated Nov. 6, 2013, Web, May 22, 2014 <http://clinicaltrials.gov/ct2/show/NCT01372943>.
Pillai et al., "Probiotics for treatment of Clostridium difficile-associated colitis in adults (Review)," Cochrane Database Syst Rev., (1):CD004611 (2008).
Porter, "Coating of pharmaceutical dosage forms," In D.B. Troy (Ed.), Remington: The Science and Practice of Pharmacy, Chapter 46, pp. 929-938 (2005).
Prakash et al., "Colon-targeted delivery of live bacterial cell biotherapeutics including microencapsulated live bacterial cells," Biologics: Targets & Therapy, 2(3):355-378 (2008).

Prevention of Sudden Infant Death Syndrome, Healthtouch.com, Thomson Micromedex, pp. 1-4, n.d., Web, Nov. 23, 2005.
Qiu et al., "Faecalibacterium prausnitzii upregulates regulatory T cells and anti-inflammatory cytokines in treating TNBS-induced colitis," Journal of Crohn's and Colitis, 7:e558-e568 (2013).
Rabeneck et al., "Bleeding and perforation after outpatient colonoscopy and their risk factors in usual clinical practice," Gastroenterology, 135(6):1899-1906 (2008).
Rager et al., "Evaluation of rumen transfaunation after surgical correction of left-sided displacement of the abomasum in cows," J. Am. Vet. Med. Assoc., 225(6):915-920 (2004).
Ramesh et al., "Prevention of Clostridium difficile-induced ileocecitis with Bacteriophage," Anaerobe, 5:69-78 (1999).
Rao et al., "Evaluation of gastrointestinal transit in clinical practice: position paper of the American and European Neurogastroenterology and Motility Societies," Neurogastroenterol. Motil., 23(1):8-23 (2011).
Rea et al., "Gut solutions to a gut problem: bacteriocins, probiotics and bacteriophage for control of Clostridium difficile infection," Journal of Medical Microbiology, 62:1369-1378 (2013).
Redelings et al., "Increase in Clostridium difficile-related mortality rates, United States, 1999-2004," Emerg Infect Dis., 13(9):1417-1419 (2007).
Response to Office Action filed Feb. 25, 2014, in European Patent Application No. 11 728 077.6.
Response to Office Action filed Jan. 28, 2015, in European Patent Application No. 11 728 077.6.
Response to Office Action filed Nov. 18, 2015, in European Patent Application No. 11 728 077.6.
Rex et al., "American College of Gastroenterology guidelines for colorectal cancer screening 2008," Am. J. Gastroenterol., 104(3):739-750 (2009).
Ricciardi et al., "Increasing prevalence and severity of Clostridium difficile colitis in hospitalized patients in the United States," Arch Surg., 142(7):624-631 (2007).
Roberts, Generation and Development Microbial Drug Products, CSO Vedanta Biosciences, 1st Microbiome Drug Development Summit, pp. 1-17 (2016).
Rodemann et al., "Incidence of Clostridium difficile infection in inflammatory bowel disease," Clin Gastroenterol Hepatol., 5(3):339-344 (2007).
Rohlke et al., "Fecal flora reconstitution for recurrent Clostridium difficile infection: results and methodology," J Clin Gastroenterol., 44(8):567-570 (2010).
Rolfe et al., "Bacterial interference between Clostridium difficile and normal fecal flora," J Infect Dis., 143(3):470-475 (1981).
Rossen et al., "Findings From a Randomized Controlled Trial of Fecal Transplantation for Patients with Ulcerative Colitis," Gastroenterology, 149(1):110-8 (2015).
Round et al., "The gut microbiota shapes intestinal immune responses during health and disease," Nat. Rev. Immunol., 9(5):313-323 (2009).
Rupnik et al., "Clostridium difficile infection: new developments in epidemiology and pathogenesis," Nat. Rev. Microbiol., 7(7):526-536 (2009).
Russell et al., "Fecal bacteriotherapy for relapsing Clostridium difficile infection in a child: a proposed treatment protocol," Pediatrics, 126(1):e239-42 (2010).
Sambol et al., "Colonization for the prevention of Clostridium difficile disease in hamsters," J. Infect. Dis., 186(12):1781-1789 (2002).
Sanchez et al., "The Role of Natural Regulatory T cells in Infection," Immunol Res., 49(0):124-134 (2011).
Sandler et al., "Possible Gut-Brain Interaction Contributing to Delayed Onset Autism Symptomatology," Fourth Int. Symp. Brain-Gut Interactions, Blackwell Science Ltd., 10(4):33 (1998).
Sandler et al., "Short-Term Benefit From Oral Vancomycin Treatment of Regressive-Onset Autism," Journal of Child Neurology, 15(7):429-435 (2000).
Sartor, "Therapeutic correction of bacterial dysbiosis discovered by molecular techniques," PNAS, 105(43):16413-16414 (2008).
Schiller, "Review article," the therapy of constipation, Ailment Pharmacol. Ther., 15:749-763 (2001).

(56) References Cited

OTHER PUBLICATIONS

Schloss, "Introducing mothur: Open-Source, Platform-Independent, Community-Supported Software for Describing and Comparing Microbial Communities," Appl. Environ. Microbiol., 75(23):7537-7541 (2009).
Schwan et al., "Relapsing Clostridium Difficile Enterocolitis Cured by Rectal Infusion of Homologous Faeces," The Lancet, 322(8354):845 (1983).
Schwan et al., "Relapsing Clostridium difficile Enterocolitis Cured by Rectal Infusion of Normal Faeces," Scand. J. Infect. Dis., 16(2):211-215 (1984).
Seeff et al., "How many endoscopies are performed for colorectal cancer screening? Results from CDC's survey of endoscopic capacity," Gastroenterology, 127:1670-1677 (2004).
Sekirov et al., "Gut microbiota in health and disease," Physiol. Rev., 90(3):859-904 (2010).
Setlow, "I Will Survive: Protecting and Repairing Spore DNA," Journal of Bacteriology, 174(9):2737-2741 (1992).
Setlow, "The bacterial spore: nature's survival package," Culture, 26(2):1-4 (2005).
Sghir et al., "Quantification of Bacterial Groups within Human Fecal Flora by Oligonucleotide Prode Hybridization," Applied and Environmental Microbiology, 66(5):2263-2266 (2000).
Shim et al., "Primary symptomless colonisation by Clostridium difficile and decreased risk of subsequent diarrhea," The Lancet, 351(9103):633-666 (1998).
Silverman et al., "Success of self-administered home fecal transplantation for chronic Clostridium difficile infection," Clin. Gastroenterol. Hepatol., 8(5):471-473 (2010).
Simor et al., "Clostridium difficile in long-term-care facilities for the elderly," Infect Control Hosp Epidemiol., 23(11):696-703 (2002).
Singh et al., "Do NSAIDs, antibiotics, infections, or stress trigger flares in IBD?" Am J Gastroenterol., 104(5):1298-1313 (2009).
Sleator, "The human superorganism—of microbes and men," Med. Hypotheses, 74(2):214-215 (2010).
Smits et al., "Therapeutic potential of fecal microbiota transplantation," Gastroenterology, 145:946-953 (2013).
Sokol et al., Faecalibacterium prausnitzii is an anti-inflammatory commensal bacterium identified by gut microbiota analysis of Crohn disease patients, Proceedings of the National Academy of Sciences, 105(43):16731-16736 (2008).
Sokol et al., "Low Counts of Faecalibacterium prausnitzii in Colitis Microbiota," Inflamm Bowel Dis., pp. 1-7 (2009).
Sunil et al., "Design and evaluation of lornoxicam bilayered tablets for biphasic release," Brazilian Journal of Pharmaceutical Sciences, 48(4):609-19 (2012).
Surawicz et al., "Treatment of refractory and recurrent Clostridium difficile infection," Nat. Rev. Gastroenterol. Hepatol., 8(6):330-339 (2011).
Surawicz, "Reining in Recurrent Clostridium difficile Infection—Who's at Risk?," Gastroenterology, 136:1152-1154 (2009).
Sutherland et al., "Lyophilized Clostridium perfringens 3 alpha- and Clostridium bifermentans 7 alpha-hydroxysteroid dehydrogenases: two new stable enzyme preparations for routine bile acid analysis," Biochim Biophys Acta, 962(1):116-121 (1988).
Takaishi et al., "Imbalance in intestinal microflora constitution could be involved in the pathogenesis of inflammatory bowel disease," J. Med. Microbiol., 298:463-472 (2008).
Takeda et al., "Serum Haloperidol Levels of Schizophrenics Receiving Treatment for Tuberculosis," Clinical Neuropharmacology, 9(4):386-397 (1986).
Tannock et al., "A new macrocyclic antibiotic, fidaxomicin (OPT-80), causes less alteration to the bowel microbiota of Clostridium difficile-infected patients than does vancomycin," Microbiology, 156(11):3354-3359 (2010).
Taras et al., "Reclassification of Eubacterium formicigenerans Holdeman and Moore 1974 as Dorea formicigenerans gen. nov., comb. nov., and description of *Dorea longicatena* sp. nov., isolated from human faeces," International Journal of Systematic and Evolutionary Microbiology, 52:423-428 (2002).

Teasley et al., "Prospective randomised trial of metronidazole versus vancomycin for Clostridium-difficile-associated diarrhoea and colitis," The Lancet, 2(8358):1043-1046 (1983).
Tilg et al., "Gut microbiome, obesity, and metabolic dysfunction," J. Clin. Invest., 121(6):2126-2132 (2011).
Tvede et al., "Bacteriotherapy for chronic relapsing Clostridium difficile diarrhea in six patients," The Lancet, 1:1156-1160 (1989).
Van Andel et al., "Interleukin-12 Has a Role in Mediating Resistance of Murine Strains to Tyzzer's Disease," Infect. Immun., 66(10):4942-4946 (1998).
van der Waaij et al., "Direct Flow Cytometry of Anaerobic Bacteria in Human Feces," Cytometry, 16:270-279 (1994).
Van Immerseel et al., "Butyric acid-producing anaerobic bacteria as a novel probiotic treatment approach for inflammatory bowel disease," Journal of Medical Microbiology, 59:141-143 (2010).
van Nood et al., "Struggling with Recurrent Clostridium difficile Infections: Is Donor Faeces the Solution?," Euro Surveill., 14(34):1-6 (2009).
van Nood, "Duodenal infusion of donor feces for recurrent Clostridium difficile," New England Journal of Medicine, 368(5):407-415 (2013).
Veldhuyzen van Zanten et al., "Drug Treatment of Functional Dyspepsia: A Systematic Analysis of Trial Methodology with Recommendations for Design of Future Trials," Am. J. Gastroenterol., 91(4):660-673 (1996).
Veldhuyzen van Zanten et al., "Validation of a 7-point Global Overall Symptom scale to measure the severity of dyspepsia symptoms in clinical trials," Ailment Pharmacol. Ther., 23(4):521-529 (2006).
Venugopal et al., "Fidaxomicin: A Novel Macrocyclic Antibiotic Approved for Treatment of Clostridium difficile Infection," Clin Infect Dis, 54(4):568-74 (2012).
Vrieze et al., "The environment within: how gut microbiota may influence metabolism and body composition," Diabetologia, 53(4):606-613 (2010).
Vulevic et al., "Modulation of the fecal microflora profile and immune function by a novel trans-galactooligosaccharide mixture (B-GOS) in healthy elderly volunteers," Am J Clin Nutr, 88:1438-46 (2008).
Wachsmann et al., "Characterization of an Orotic Acid Fermenting Bacterium, Zymobacterium oroticum, nov. gen., nov. spec.," Journal of Bacteriology, 68(4):400-404 (1954).
Walter et al., "Host-microbial symbiosis in the vertebrate gastrointestinal tract and the Lactobacillus reuteri paradigm," PNAS USA, 108(Suppl 1):4645-4652 (2011).
Warny et al., "Toxin production by an emerging strain of Clostridium difficile associated with outbreaks of severe disease in North America and Europe," Lancet, 366(9491):1079-84 (2005).
Warren et al., "*Clostridium aldenense* sp. nov. and *Clostridium citroniae* sp. nov. Isolated from Human Clinical Infections," Journal of Clinical Microbiology, 44(7):2416-2422.
Wasfy et al., "Comparison of Preservation Media for Storage of Stool Samples," Journal of Clinical Microbiology, 33(8):2176-2178 (1995).
Weingarden et al., "Dynamic changes in short- and long-term bacterial composition following fecal microbiota transplantation for recurrent Clostridium difficile infection," Microbiome, 3(10), 8 pages (2015).
Weissman et al., "Stool Transplants: Ready for Prime Time?," Current Gastroenterology Reports, 14:313-316 (2012).
Wells et al., "Clostridia: Sporeforming Anaerobic Bacilli," Medical Microbiology—NCBI Bookshelf, 4th Edition, Chapter 18, pp. 1-20 (1996) <https://www.ncbi.nlm.nih.gov/books/NBK8219/?report=printable>.
Wenisch et al., "Comparison of Vancomycin, Teicoplanin, Metronidazole, and Fusidic Acid for the Treatment of Clostridium difficile-Associated Diarrhea," Clin Infect Dis., 22(5):813-818 (1996).
Wettstein et al., "Fecal Bacteriotherapy—An effective Treatment for Relapsing Symptomatic Clostridium difficile Infection," Abstract, 15th United European Gastroenterology Week (UEGW) Poster presentations, United European Gastroenterology Federation, France, A303 (2007).
Wettstein et al., "Skewered diverticulum: another cause of abdominal pain," Internal Med J, 31(8):495-496 (2001).

(56) References Cited

OTHER PUBLICATIONS

Wikoff et al., "Metabolomics analysis reveals large effects of gut microflora on mammalian blood metabolites," PNAS, 106(10):3698-3703 (2009).
Wilson et al., "Human Colonic Biota Studied by Ribosomal DNA Sequence Analysis," Appl. Environ. Microbiol., 62(7):2273-2278 (1996).
Yoon et al., "Treatment of Refractory/Recurrent C. difficile-associated Disease by Donated Stool Transplanted Via Colonoscopy: A Case Series of 12 patients," J Clin Gastroenterol., 44(8):562-566 (2010).
You et al., "Successful treatment of fulminant Clostridium difficile infection with fecal bacteriotherapy," Ann. Intern. Med., 148(8):632-633 (2008).
Yue et al., "Similarity Measure Based on Species Proportions," Commun. Stat. Theor. Methods, 34(11):2123-2131 (2005).
Zar et al., "A Comparison of Vancomycin and Metronidazole for the Treatment of Clostridium difficile-Associated Diarrhea, Stratified by Disease Severity," Clin Infect Dis., 45(3):302-307 (2007).
Zhou et al., "Total fecal microbiota transplantation alleviates high-fat diet-induced steatohepatitis in mice via beneficial regulation of gut microbiota," Scientific Reports (Nature), 7(1529):1-11 (2017).
Zilberberg et al., "Clostridium difficile Infections among Hospitalized Children, United States, 1997-2006," Emerg. Infect. Dis, 16(4):604-609 (2010).
Zilberberg et al., "Clostridium difficile-related Hospitalizations among US Adults, 2006," Emerg. Infect. Dis, 15(1):122-124 (2009).
Zilberberg et al., "Increase in Adult Clostridium difficile-related Hospitalizations and Case-Fatality Rate, United States, 2000-2005," Emerg. Infect. Dis, 14(6):929-931 (2008).
Zilberberg et al., "Increase in Clostridium difficile-related Hospitalizations Among Infants in the United States, 2000-2005," Pediatr Infect Dis J., 27(12):1111-1113 (2008).
Zoppi et al., "Oral Bacteriotherapy in Clinical Practice," Eur J. Pediatr, 139(1):18-21 (1982).
Zoppi et al., "Oral Bacteriotherapy in Clinical Practice," Eur J. Pediatr, 139(1):22-24 (1982).
Zoppi et al., "The Intestinal Ecosystem in Chronic Functional Constipation," ACTA Paediatr, Scandinavian University Press, p. 836-841 (1998).
Eller et al., "Anaerobic Roll Tube Media for Nonselective Enumeration and Isolation and Bacteria in Human Feces," Applied Microbiology 1971, vol. 22, p. 522-529.
Extended European Search Report dated Mar. 16, 2018, in European Patent Application No. 17203052.0.
International Search Report and Written Opinion (WO) dated Jan. 17, 2018, in International Application No. PCT/US2017/045092.
International Search Report and Written Opinion (WO) dated Feb. 2, 2018 in International Application No. PCT/US2017/055618.
International Search Report and Written Opinion (WO) dated Feb. 2, 2018 in International Application No. PCT/US2017/056131.
International Search Report and Written Opinion (WO) dated Jan. 31, 2018 in International Application PCT/US2017/056126.
International Search Report and Written Opinion (WO) dated Feb. 21, 2018 inInternational Application No. PCT/US2017/056129.
Lee et al., "The outcome and long-term follow-up of 94 patients with recurrent and refractory *Clostridium difficile* infection using single to multiple fecal microbiota transplantation vie retention enema," *European Journal Clinical Microbiology Infect Dis.*, 33:1425-1428 (2014).
Manichanh et al., "Reshaping the gut microbiome with bacterial transplantation and antibiotic intake," Genome Research 20:1411-1419 (2010).
Paterson et al., "Putting back the bugs: Bacterial treatment relieves chronic diarrhoea," Med J Aus, 160:232-233 (1994).
Sullivan et al., "Effect of supplement with lactic-acid producing bacteria on fatigue and physical activity in patients with chronic fatigue syndrome," Nutritional Journal, 8(4):1-6 (2009).
Vaughn et al., "Novel treatment options for ulcerative colitis," *Future Science*, 1-20 (2013).
Youngster et al., "Oral, Capsulized, Frozen Microbiota Transplantation for Relapsing *Clostridium difficile* Infection," *American Medical Association*, 312 (174) 1772-1778 (2014).

* cited by examiner

COMPOSITIONS AND METHODS FOR TRANSPLANTATION OF COLON MICROBIOTA

CROSS-REFERENCE TO RELATED APPLICATIONS

This application is a continuation of U.S. application Ser. No. 15/261,319 filed Sep. 9, 2016, which is a continuation of U.S. application Ser. No. 14/003,411 filed Jan. 17, 2014, which is a 371 of International Application No. PCT/US2012/028484 filed Mar. 9, 2012, which claims the benefit of U.S. Provisional Application No. 61/450,838 filed Mar. 9, 2011, the entireties of each of which are herein incorporated by reference. This application is also a continuation of U.S. application Ser. No. 15/173,134 filed Jun. 3, 2016, which is a continuation of U.S. application Ser. No. 14/003,411 filed Jan. 17, 2014, which is a 371 of International Application No. PCT/US2012/028484 filed Mar. 9, 2012, which claims the benefit of U.S. Provisional Application Ser. No. 61/450,838, filed Mar. 9, 2011, the entireties of each of which are herein incorporated by reference.

GOVERNMENT FUNDING

This invention was made with government support under AI091907 awarded by the National Institutes of Health. The government has certain rights in the invention.

BACKGROUND

In 1978, *Clostridium difficile* was first recognized as a major cause of diarrhea and pseudomembranous colitis associated with the use of antimicrobial agents. Since this time, infection by *C. difficile* has been steadily growing in incidence, morbidity, and mortality across North America and Europe (Freeman et al. Clin Microbiol Rev 2010; 23:529-49; Kelly and LaMont, N Engl J Med 2008; 359: 1932-40). Analysis of the U.S. National Hospital Discharge Survey statistics between 1996 and 2003 reveals a doubling in the prevalence of diagnosis of *C. difficile* infection (CDI), to 0.61/1,000, among inpatients (McDonald et al. Emerg Infect Dis 2006; 12:409-15). A 2008 survey of 12.5% of all U.S. acute care facilities indicated a CDI prevalence rate of 13.1/1,000, which is at least an order of magnitude higher than that found previously (Jarvis et al. Am J Infect Control 2009; 37:263-70). While older patients have disproportionately greater rates of CDI than younger individuals, no age group is spared, and the incidence of CDI-related hospitalizations has been rising even in the pediatric population (Zilberberg et al. Emerg Infect Dis 2010; 16:604-9). The increase in incidence has been further compounded by an elevated frequency of the most severe forms of this disease, as evidenced by rising CDI-associated morbidity and case fatality (Ricciardi et al. Arch Surg 2007; 142:624-31; discussion 631, Zilberberg et al. Emerg Infect Dis 2008; 14:929-31). This is, in part, related to the emergence of more virulent *C. difficile* strains, such as PCR ribotype 027/North American Pulsed Field type 1 (NAP1), which is characterized by a greater potential for toxin production and antibiotic resistance than other clinically-relevant strains (Rupnik et al. Nat Rev Microbiol 2009; 7:526-36, Kuijper et al. Euro Surveill 2008; 13).

Recurrent CDI is one of the most difficult and increasingly common challenges associated with CDI (Surawicz, Gastroenterology 2009; 136:1152-4). An initial incidence of CDI can be followed by a relapse within 30 days in about 20-30% of cases (Kelly and LaMont, N Engl J Med 2008; 359:1932-40 (2008); Louie et al. N Engl J Med 2011; 364:422-31; Pepin et al. Clin Infect Dis 2006; 42:758-64), and the risk of recurrence doubles after two or more occurrences (McDonald et al. Emerg Infect Dis 2006; 12:409-15). Older age, intercurrent antibiotic use for non-*C. difficile* indications, renal insufficiency, immune deficiency, and antacid medications, are some of the known risk factors for recurrent CDI (Surawicz, Gastroenterology 2009; 136:1152-4, Garey et al. J Hosp Infect 2008; 70:298-304). The presence of just three clinical criteria: age >65 years, severe disease, and continued use of antibiotics after treating the initial CDI episode, are predictive of an almost 90% relapse rate (Hu et al. Gastroenterology 2009; 136:1206-14). CDI also commonly complicates management of inflammatory bowel disease (IBD), which has recently been recognized as an additional independent risk factor for CDI infection (Issa et al. Clin Gastroenterol Hepatol 2007; 5:345-51, Rodemann et al. Clin Gastroenterol Hepatol 2007; 5:339-4415). CDI in patients with underlying IBD is associated with increased severity of colitis and higher rates of recurrence and colectomy (Issa et al. Inflamm Bowel Dis 2008; 14:1432-42).

It is now recognized that the presence of normal, healthy, intestinal microbiota (normal gut microorganisms) offers protection against CDI. Conversely, severe disruption of normal intestinal microbiota by use of antibiotics, including metronidazole and vancomycin that are used to treat CDI, is likely one of the major reason for its recurrence. Chang and colleagues used 16S rDNA sequencing to analyze the fecal microbiota of seven patients with initial and recurrent CDI (Chang et al. J Infect Dis 2008; 197:435-8). They reported that bacterial species diversity was reduced in all patients compared to normal control subjects. The greatest reduction in species diversity, however, was found in the three patients with recurrent CDI and disruption of their gut microbiota was evident at the phylum level—with marked reduction in Bacteroidetes, normally one of the two dominant phyla in the colon. Instead, the gut microbiota in these patients were dominated by members of the proteobacteria and verrucomicrobia phyla, which normally are only minor constituents of the colon microbiota.

The general aim of antibiotic treatment for recurrent CDI is not mere suppression of *C. difficile*, but also preservation of the residual colon microbiota and optimization of their restoration. Various antibiotic regimens, including long tapered or pulsed dosing with vancomycin (McFarland et al., Am J Gastroenterol 2002; 97:1769-75) and rifaximin "chaser" protocols (Johnson et al. Clin Infect Dis 2007; 44:846-8, Johnson et al. Anaerobe 2009; 15:290-1) have been used to achieve this objective with partial success. Recently, fidaxomicin, a new macrocyclic antibiotic which is narrow in spectrum and spares *Bacteroides* species, was shown to reduce the initial relapse rate of CDI by 50% compared to vancomycin treatment (Louie et al. N Engl J Med 2011; 364:422-31). However, treatment with fidaxomicin did not alter the recurrence rate of CDI caused by the more virulent PCR 027/NAP1 strain. Therefore, despite these advances it seems likely that the challenges in treatment of recurrent CDI will remain for the foreseeable future.

Fecal microbiota transplantation (FMT), also commonly known as 'fecal bacteriotherapy' represents the one therapeutic protocol that allows the fastest reconstitution of a normal composition of colon microbial communities. For many decades, FMT has been offered by select centers across the world, typically as an option of last resort for patients with recurrent CDI. The mostly commonly earliest cited report for FMT was by Eiseman and colleagues who in 1958 described the use of fecal enemas for patients who likely had severe or fulminant form of pseudomembranous colitis (Eiseman et al. Surgery 1958; 44:854-9). Since this time, well over 200 cases have been reported as individual case reports, or small case series, with a ~90% cumulative success rate in clearing recurrent CDI, without any noted adverse events. The history and general methodology used for FMT have been described in several recent reviews (Bakken. Anaerobe 2009; 15:285-9, van Nood et al. Euro Surveill 2009; 14, Khoruts and Sadowsky. Mucosal Immunol 2011; 4:4-7). However, despite the long and successful track record, as well as great clinical need, the availability of the procedure for many patients remains very limited.

The lack of wider practice of FMT is due in large part to multiple non-trivial practical barriers and not due to lack of efficacy. These include lack of reimbursement for donor screening, lack of adequate donors at the correct time, difficulty in material preparation and administration, as well as aesthetic concerns about doing the procedure in endoscopy or medical office. These also include patient perception of the procedure, willingness of staff to perform the procedure, sanitation issues related to manipulation of fecal matter. Together these factors make it a distasteful option that is often considered a treatment of last resort, and that is largely unavailable to the vast majority of patients who could benefit from it. Moreover, the pharmaceutical industry has shown little interest in technological development of FMT-based therapeutics, in large part due to the wide availability of donor material and its complex composition. Instead, development has been driven mostly by individual clinicians faced with desperate need in their patients.

SUMMARY OF THE INVENTION

The present invention provides compositions that include an extract or a preparation of human feces. In one embodiment, a composition includes no greater than 0.05%, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, or 10% weight non-living material/weight biological material. Optionally the biological material includes human gut, colon or intestinal fecal microbes, and optionally the biological material includes human gut, colon or intestinal bacteria. Optionally the composition includes a pharmaceutically acceptable carrier. Optionally the composition is a formulation for oral administration.

In one embodiment, a composition consists of, or consists essentially of, particles of non-living material and/or particles of biological material that will pass through a sieve having a sieve size of 2.0 mm, 1.0 mm, 0.5 mm, 0.25 mm, 0.212 mm, 0.180 mm, 0.150 mm, 0.125 mm, 0.106 mm, 0.090 mm, 0.075 mm, 0.063 mm, 0.053 mm, 0.045 mm, 0.038 mm, 0.032 mm, 0.025 mm, 0.020 mm, 0.01 mm, or 0.2 mm. Optionally the composition includes a pharmaceutically acceptable carrier, and optionally the composition is a formulation for oral administration.

In one embodiment, a composition includes at least 4 different phyla of gut, colon or intestinal bacteria extracted or prepared from the gut, colon or intestine, wherein the phyla include a member of Bacteroidetes phylum, member of Firmicutes phylum, member of Proteobacteria phylum, member of Tenericutes phylum, or a combination thereof. Optionally the phyla are chosen from Bacteroidetes, Firmicutes, Proteobacteria, and Tenericutes. The composition includes no greater than 0.05%, 0.1%, 0.2%, 0.3%, 0.4%, 0.5%, 0.6%, 0.7%, 0.8%, 0.9% 1%, 2%, 3%, 4%, 5%, 6%, 7%, 8%, 9%, or 10% weight non-living material/weight biological material. Optionally the biological material includes human gut, colon or intestinal flora. Optionally the biological material includes human gut, colon or intestinal bacteria. Optionally the composition includes a pharmaceutically acceptable carrier, and optionally the composition is a formulation for oral administration.

In one embodiment, a composition includes an extract of human feces wherein the composition is substantially odorless, optionally includes biological material, and optionally wherein the biological material includes bacteria. Optionally the composition includes a pharmaceutically acceptable carrier, and optionally the composition is a formulation for oral administration.

A composition of the present invention may include no greater than 0.1% weight non-living material/weight biological material. In one embodiment, a composition may consist of, or consist essentially of, particles that will pass through a 0.25 mm sieve, or equivalent. In one embodiment, a composition may include no greater than 0.05%, 0.1%, 0.2%, 0.3%, 0.4%, 0.5%, 0.6%, 0.7%, 0.8%, 0.9%, 1%, 2%, 3%, 4% 5%, 6%, 7%, 8%, 9% or 10% weight non-living material/weight biological material. A composition of the present invention may further include a cryoprotectant, such as glycerol. In one embodiment, a composition may be at a temperature of less than 0° C. In one embodiment, a composition is a solid, such as a powder. A composition of the present invention may include at least $1\times10^{10}$, $2\times10^{10}$, $3\times10^{10}$, $4\times10^{10}$, or $5\times10^{10}$ bacteria. In one embodiment, the biological material of a composition may include a plurality of prokaryotic cells, eukaryotic cells, or viruses; or a population of prokaryotic cells, eukaryotic cells, and viruses, that is substantially identical to or representative of or equivalent to a population of prokaryotic cells, eukaryotic cells, and viruses present in a feces of a normal healthy human. In one embodiment, the biological material of a composition may include a population of prokaryotic cells and viruses that is substantially identical to or representative of or equivalent to a population of prokaryotic cells and viruses present in the feces of a normal healthy human. In one embodiment, the biological material of a composition includes a population of prokaryotic cells, eukaryotic cells, or viruses that is substantially identical to or representative of or equivalent to a population of prokaryotic cells, eukaryotic cells, and viruses present in the feces of a normal healthy human.

The present invention also provides composition prepared by a process. In one embodiment, a process includes subjecting a fecal sample to a condition or conditions that remove at least 91%, 92%, 93%, 94% 95%, 96%, 97%, 98%, 99% or more of the non-living material present in the fecal sample. In one embodiment, a process includes filtering a fecal sample with a filter medium, wherein the filter medium includes a sieve size of no greater than 2.0 mm, 1.0 mm, 0.5 mm, 0.25 mm, 0.212 mm, 0.180 mm, 0.150 mm, 0.125 mm, 0.106 mm, 0.090 mm, 0.075 mm, 0.063 mm, 0.053 mm, 0.045 mm, 0.038 mm, 0.032 mm, 0.025 mm, 0.020 mm, 0.01 mm, or 0.2 mm to result in or to generate a filtrate. Optionally a composition includes a biological material, and optionally the biological material includes bacteria. Optionally a composition includes a pharmaceutically acceptable carrier. Optionally a composition is a formulation for oral administration. Optionally the process may occur at a temperature of no greater than 26° C., 27° C., 28° C., 29° C., 30° C., 31° C., 32° C., 33° C., or 34° C.

The composition may include at least 4 different phyla of bacteria, wherein the include a member of Bacteroidetes phylum, member of Firmicutes phylum, member of Proteobacteria phylum, member of Tenericutes phylum, or a combination thereof. Optionally the phyla are chosen from Bacteroidetes, Firmicutes, Proteobacteria, and Tenericutes. In one embodiment, the composition further includes at least 5, 6, 7, 8, 9, or 10 different classes of bacteria chosen from Actinobacteria, Bacteroidia, Bacilli, Clostridia, Erysipelotrichi, Alphaproteobacteria, Betaproteobacteria, Gammaproteobacteria, Mollicutes, and Verrucomicrobiae.

The process may further include adding a cryoprotectant, for instance, glycerol, to the composition. The process may further include freezing the composition. The composition may be for use as a therapeutic agent, and it may be for use in the treatment of a disease or a pathological or iatrogenic condition of the colon. The disease may be a disease or condition characterized by a dysfunctional or pathological composition of colon microbiota, for instance, a *Clostridium difficile* colitis.

The present invention also provides a method for replacing or supplementing or modifying a subject's colon microbiota. The method may include administering to the subject a composition described herein. The present invention also provides a method for treating a subject. The method may include administering to a subject in need thereof an effective amount of a composition described herein. The methods may further include removal of some, most, or substantially all of the subject's colon, gut or intestinal microbiota prior to the administering. The subject may have or be at risk for having a colitis. In one embodiment, the colitis is an autoimmune colitis, such as an inflammatory bowel disease, an ulcerative colitis, a Crohn's disease, or an irritable bowel syndrome. In one embodiment, the colitis is an infectious colitis, such as a *Clostridium difficile* colitis or an enterohemorrhagic colitis. The *Clostridium difficile* colitis may be an acute *Clostridium difficile* colitis, a relapsing *Clostridium difficile* colitis, and a severe *Clostridium difficile* colitis. The enterohemorrhagic colitis may be caused by a *Shigella* spp. or an *E. coli*. The subject may have or be at risk for chronic diarrhea or chronic constipation.

The present invention also provides the use of a composition described herein for the manufacture of a medicament, or for the manufacture of a medicament for treating or ameliorating or preventing a disease or a pathological or iatrogenic condition of the colon. Optionally the disease is a disease or condition characterized by a dysfunctional or pathological composition of colon microbiota, or the disease is a *Clostridium difficile* colitis, or the disease or condition is a colitis, an autoimmune colitis, an infectious colitis or an enterohemorrhagic colitis.

The term "and/or" means one or all of the listed elements or a combination of any two or more of the listed elements.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

Unless otherwise specified, "a," "an," "the," and "at least one" are used interchangeably and mean one or more than one.

Also herein, the recitations of numerical ranges by endpoints include all numbers subsumed within that range (e.g., 1 to 5 includes 1, 1.5, 2, 2.75, 3, 3.80, 4, 5, etc.).

For any method disclosed herein that includes discrete steps, the steps may be conducted in any feasible order. And, as appropriate, any combination of two or more steps may be conducted simultaneously.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

DETAILED DESCRIPTION OF ILLUSTRATIVE EMBODIMENTS

Figure 1:
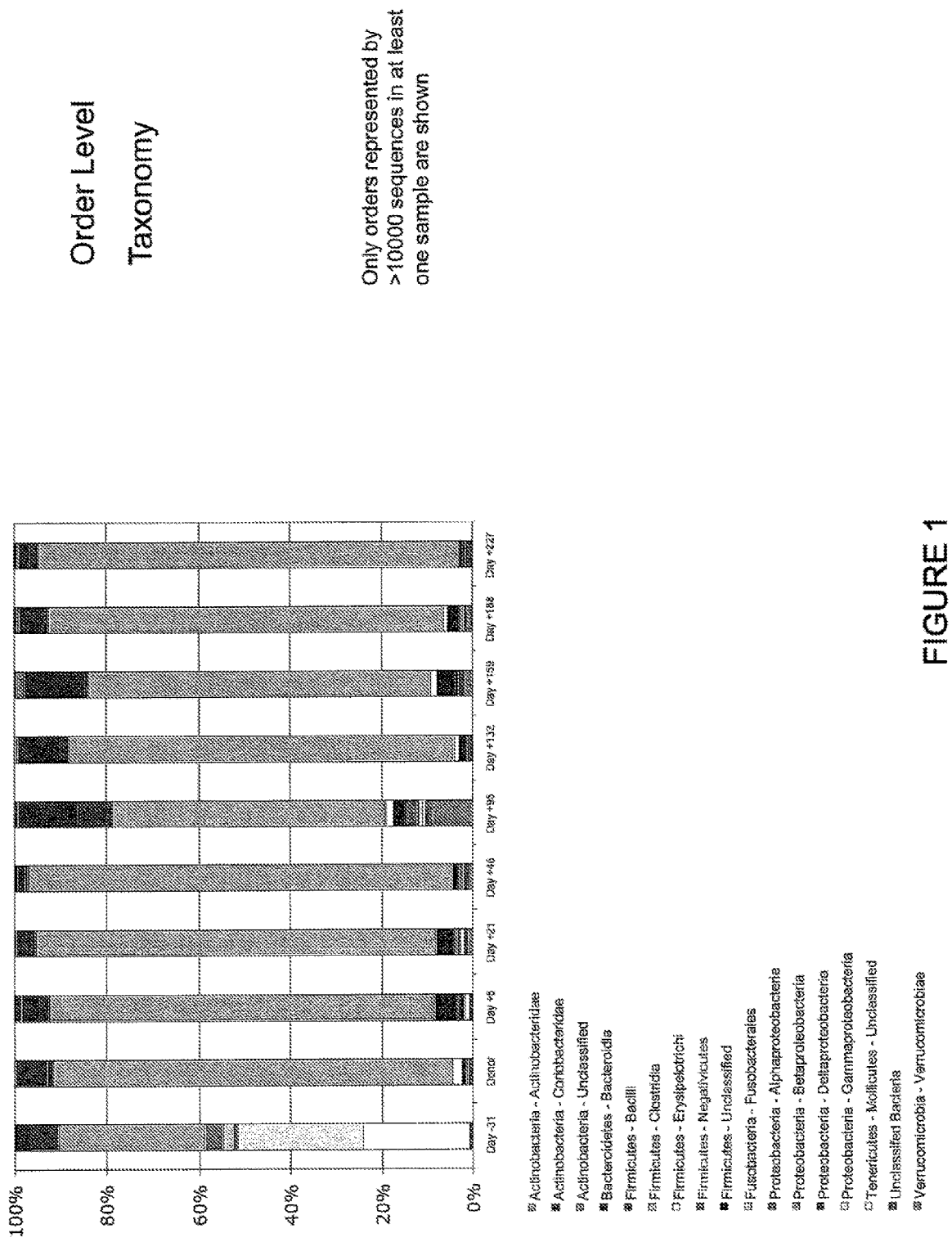
FIG. 1 is a plot of microbial community taxonomic distribution at the order level in a fecal transplant bacteriotherapy recipient before and after receiving the transplant in accordance with Example 1.

Before the present invention standard practices suggested matching each recipient of fecal bacteriotherapy with a separate donor, usually a close family member, or using the recipient's own banked feces for later use. The rationale for these practices was the idea that close family members have already shared their pathogens, and that these kinds of gut microbiota would be somehow better tolerated by the recipient's immune system because of previous exposure. However, this resulted in duplicative screening, burdening already debilitated patients with the task of finding a suitable donor, pressure on the donor to provide the material and potentially withholding important medical information, pressure to decrease costs since costs were usually borne by the patient, time delays associated with the screening, and pressure to accept donors of suboptimal health status during donor selection. The compositions presented herein result from a more standardized manufacturing process with rigorous donor screening, multiple steps of filtration that concentrate the microbiota and remove the bulk of nonliving material, and optionally freeze/thaw it in a way that preserves its viability. The compositions presented herein provide a significant advantage by making useful compositions of colon microflora readily available for use by a physician to treat a patient. Moreover, it is much more aesthetically acceptable, as the compositions are nearly odorless, are in concentrated form, and are easily manipulated using standard laboratory practice.

The present invention provides compositions that include fecal microbes. As used herein, the term "fecal microbes" refers to microorganisms that are present in the gut, intestine, or colon, preferably colon, of a normal healthy adult human. Such a composition may be prepared by processing fecal material. As used herein, the term "fecal material" refers to human stool. Unprocessed fecal material contains non-living material and biological material. The "non-living material" may include, but is not limited to, dead bacteria, shed host cells, proteins, carbohydrates, fats, minerals, mucus, bile, undigested fiber and other foods, and other compounds resulting from food and metabolic waste products and partial or complete digestion of food materials. "Biological material" refers to the living material in fecal material, and includes microbes including prokaryotic cells such as bacteria and archea (e.g., living prokaryotic cells and spores that can sporulate to become living prokaryotic cells), eukaryotic cells such as protozoa and fungi, and viruses. In one embodiment, "biological material" refers to the living material, e.g., the microbes, eukaryotic cells, and viruses, that are present in the colon of a normal healthy human.

Examples of prokaryotic cells that may be present in a composition of the present invention include cells that are members of the class Actinobacteria, such as the subclass Actinobacteridae or Coriobacteridae, such as the order Bifidobacteriales or Coriobacteriales, and/or such as the family Bifidobacteriaceae or Coriobacteriaceae; members of the phylum Bacteroidetes, such as class Bacteroidia, such as class Bacteroidales, and/or such as family Bacteroidaceae or Rikenellaceae; members of the phylum Firmicutes, such as class Bacilli, Clostridia, or Erysipelotrichi, such as order Bacillales or Lactobacillales or Clostridales or Erysipelotrichales, and/or such as family Paenibacillaceae or Aerococcaceae or Lactobacillaceae or Streptococcaceae or Catabacteriaceae or Peptococcaceae or Peptostreptococcaceae or Ruminococcaceae or Clostridiaceae or Eubacteriaceae or Lachnospiraceae or Erysipelotrichaceae; members of the phylum Proteobacteria, such as class Alphaproteobacteria or Betaproteobacteria or Gammaproteobacteria, such as order Rhizobiales or Burkholderiales or Alteromonadales or Enterobacteriales, and/or such as family Rhodobiaceae or Burkholderiaceae or Shewanellaceae or Enterobacteriaceae; members of the phylum Tenericutes, such as the class Mollicutes, such as the order Entomoplasmatales, and/or such as the family Spiroplasmataceae; and/or members of the class Verrucomicrobiae, such as the order Verrucomicrobiales, and/or such as the family Verrucomicrobiaceae.

In one embodiment a composition of the present invention may include prokaryotic bacteria that are members of at least 1 phylum, at least 2 phyla, at least 3 phyla, at least 4 phyla, at least 5 phyla, at least 6 phyla, at least 7 phyla, at least 8 phyla, at least 9 phyla, or at least 10 phyla. In one embodiment a composition of the present invention may include prokaryotic bacteria that are members of at least 1 class, at least 2 classes, at least 3 classes, at least 4 classes, at least 5 classes, at least 6 classes, or at least 7 classes. In one embodiment a composition of the present invention may include prokaryotic bacteria that are members of at least 1 order, at least 2 orders, at least 3 orders, at least 4 orders, at least 5 orders, at least 6 orders, or at least 7 orders. In one embodiment a composition of the present invention may include prokaryotic bacteria that are members of at least 1 family, at least 2 families, at least 3 families, at least 4 families, at least 5 families, at least 6 families, at least 7 families. In one embodiment a composition of the present invention may include at least 5, at least 10, at least 20, or at least 30 different genera of prokaryotic bacteria. In one embodiment a composition of the present invention may include at least 10, at least 50, at least 100, at least 200, at least 300, or at least 400 different species of prokaryotic bacteria.

In one embodiment a composition of the present invention includes no greater than 5% weight of non-living material/ weight biological material (wt/wt), no greater than 2.5% (wt/wt), no greater than 1% (wt/wt), no greater than 0.1% (wt/wt), no greater than 0.01% (wt/wt), or no greater than 0.001% (wt/wt) nonliving material. In one embodiment, the amount of non-living material in a composition of the present invention is undetectable using currently available techniques. For instance, living material can be stained for biological activity, electron transport, DNA and RNA for specific genes.

In one embodiment, the fecal material present in a composition of the present invention does not include particles (e.g., particles of non-living material and/or particles of biological material) having a size of greater than 2.0 millimeters (mm), greater than 1.0 rnm, greater than 0.5 mm, greater than 0.25 mm, greater than 0 212 mm, greater than 0.180 mm, greater than 0.150 mm, greater than 0.125 mm, greater than 0.106 rnm, greater than 0.090 mm, greater than 0.075 mm, greater than 0.063 mm, greater than 0.053 mm, greater than 0.045 mm, greater than 0.038 mm, greater than 0.032 mm, greater than 0.025 mm, greater than 0.020 mm, greater than 0.01 mm, or greater than 0.2 mm. Non-fecal material present in a composition may include particles having a size of greater than 2.0 mm, greater than 1.0 nun, greater than 0.5 mm, greater than 0.25 mm, greater than 0.212 mm, greater than 0.180 mm, greater than 0.150 mm, greater than 0.125 mm, greater than 0.106 mm, greater than 0.090 mm, greater than 0.075 mm, greater than 0.063 mm, greater than 0.053 mm, greater than 0.045 mm, greater than 0.038 mm, greater than 0.032 mm, greater than 0.025 mm, greater than 0.020 mm, greater than 0.01 mm, or greater than 0.2 mm. In one embodiment, the fecal material present in a composition of the present invention consists of, or consists essentially of, particles of non-living material and/or biological material having a size that will pass through a sieve having a sieve size of 2.0 nun, 1.0 mm, 0.5 mm, 0.25 mm, 0.212 mm, 0.180 mm, 0.150 mm, 0.125 mm, 0.106 mm, 0.090 mm, 0.075 mm, 0.063 mm, 0.053 mm, 0.045 mm, 0.038 mm, 0.032 mm, 0.025 mm, 0.020 mm, 0.01 mm, or 0.2 mm. Thus, in such an embodiment, the fecal material present in a composition has a size that is less than or equal to 2.0 mm, less than or equal to 1.0 mm, less than or equal to 0.5 mm, less than or equal to 0.25 mm, less than or equal to 0.212 mm, less than or equal to 0.180 mm, less than or equal to 0.150 mm, less than or equal to 0.125 mm, less than or equal to 0.106 mm, less than or equal to 0.090 mm, less than or equal to 0.075 mm, less than or equal to 0.063 mm, less than or equal to 0.053 mm, less than or equal to 0.045 mm, less than or equal to 0.038 mm, less than or equal to 0.032 mm, less than or equal to 0.025 mm, less than or equal to 0.020 mm, less than or equal to 0.01 mm, or less than or equal to 0.2 mm. The sieve size may be based on the US Standard sieve sizes of, for instance, 10, 18, 35, 60, 70, 80, 100, 120, 140, 170, 200, 230, 270, 325, or 400.

A composition of the present invention may optionally include a cryoprotectant. A cryoprotectant is a compound that maintains the viability of fecal microbes when frozen. Cryoprotectants are known in the art and used routinely to protect microbes when exposed to freezing conditions. Examples include, but are not limited to, amino acids such as alanine, glycine, proline; simple sugars such as sucrose, glucose, lactose, ribose, and trehalose; and other compounds such as dimethyl sulfoxide (DMSO), and glycerol. The amount of cryoprotectant present in a composition described herein may vary depending on the cryoprotectant used and the temperature to be used for freezing (e.g., −20° C., −80° C., or a different temperature). The amount of cryoprotectant that can be used is known to the skilled person or may be easily determined using routine experimentation. In one embodiment, a composition of the present invention may include glycerol at a concentration of 10%.

In one embodiment a composition of the present invention does not include pathogenic biological material. In one embodiment, fecal material is from a person that has undergone a medical history, a physical examination, and laboratory testing. The evaluation of medical history may include, but is not limited to, risk of infectious agents, presence of gastrointestinal co-morbidities, factors that can or do affect the composition of the intestinal microbiota, and systemic medical conditions. Exclusion criteria regarding risk of infectious agents may include, but are not limited to, known viral infection with Hepatitis B, C or HIV; known exposure to HIV or viral hepatitis at any time; high risk behaviors including sex for drugs or money, men who have sex with men, more than one sexual partner in the preceding 12 months, any past use of intravenous drugs or intranasal cocaine, history of incarceration; tattoo or body piercing within 12 months; travel to areas of the world where risk of traveler's diarrhea is higher than the US; and current communicable disease, e.g., upper respiratory viral infection.

Exclusion criteria regarding gastrointestinal co-morbidities include, but are not limited to, history of irritable bowel syndrome, wherein specific symptoms may include frequent abdominal cramps, excessive gas, bloating, abdominal distension, fecal urgency, diarrhea, constipation; history of inflammatory bowel disease such as Crohn's disease, ulcerative colitis, microscopic colitis; chronic diarrhea; chronic constipation or use of laxatives; history of gastrointestinal malignancy or known colon polyposis; history of any abdominal surgery, e.g., gastric bypass, intestinal resection, appendectomy, cholecystectomy, and the like; use of probiotics or any other over the counter aids used by the potential donor for purpose of regulating digestion, but yogurt and kefir products may be allowed if taken merely as food rather than nutritional supplements.

Exclusion criteria regarding factors that can or do affect the composition of the intestinal microbiota include, but are not limited to, antibiotics for any indication within the preceding 6 months; any prescribed immunosuppressive or anti-neoplastic medications.

Exclusion criteria regarding systemic medical conditions include, but are not limited to, established or emerging metabolic syndrome, where criteria used for definition here are stricter than established criteria, including history of increased blood pressure, history of diabetes or glucose intolerance; known systemic autoimmunity, e.g., connective tissue disease, multiple sclerosis; known atopic diseases including asthma or eczema; chronic pain syndromes including fibromyalgia, chronic fatigue syndrome; ongoing (even if intermittent) use of any prescribed medications, including inhalers or topical creams and ointments; neurologic, neurodevelopmental, and neurodegenerative disorders including autism, Parkinson's disease.

Exclusion criteria on physical examination may include, but are not limited to, general, such as body mass index >26 $kg/m^2$, central obesity defined by waste:hip ratio >0.85 (male) and >0.80 (female); blood pressure >135 mmHg systolic and >85 mmHg diastolic; skin—presence of a rash, tattoos or body piercing placed within a year, jaundice; enlarged lymph nodes; wheezing on auscultation; hepatomegaly or *stigmata* of liver disease; swollen or tender joints; muscle weakness; abnormal neurologic examination.

Exclusion criteria on laboratory testing may include, but is not limited to, positive stool *Clostridium difficile* toxin B tested by PCR; positive stool cultures for any of the routine pathogens including *Salmonella, Shigella, Yersinia, Campylobacter, E. coli* 0157:H7; abnormal ova and parasites examination; positive *Giardia, Cryptosporidium,* or *Helicobacter pylori* antigens; positive screening for any viral illnesses, including HIV 1 and 2, Viral Hepatitis A IgM, Hepatitis surface antigen and core Ab; abnormal RPR (screen for syphilis); any abnormal liver function tests including alkaline phosphatase, aspartate aminotransaminase, alanine aminotransferase; raised serum triglycerides >150 mg/dL; HDL cholesterol <40 mg/dL (males) and <50 mg/dL (females); high sensitivity CRP >2.4 mg/L; raised fasting plasma glucose (>100 mg/dL).

The compositions of the present invention may be included in a diversity of pharmaceutically acceptable formulations. In one embodiment, a formulation may be a fluid composition. Fluid compositions include, but are not limited to, solutions, suspensions, dispersions, and the like. In one embodiment, a formulation may be a solid composition. Solid compositions include, but are not limited to, powder, granule, compressed tablet, pill, capsule, chewing gum, wafer, and the like. Those formulations may include a pharmaceutically acceptable carrier to render the composition appropriate for administration to a subject. As used herein "pharmaceutically acceptable carrier" includes pharmacologically inactive compounds compatible with pharmaceutical administration. The compositions of the present invention may be formulated to be compatible with its intended route of administration. A composition of the present invention may be administered by any method suitable for depositing in the gastrointestinal tract, preferably the colon, of a subject. Examples of routes of administration include rectal administration (e.g., by suppository, enema, upper endoscopy, upper push enteroscopy, or colonoscopy), intubation through the nose or the mouth (e.g., by nasogastric tube, nasoenteric tube, or nasal jejunal tube), or oral administration (e.g., by a solid such as a pill, tablet, or capsule, or by liquid).

For therapeutic use in the method of the present invention, a composition may be conveniently administered in a form containing one or more pharmaceutically acceptable carriers. Suitable carriers are well known in the art and vary with the desired form and mode of administration of the composition. For example, they may include diluents or excipients such as fillers, binders, wetting agents, disintegrators, surface-active agents, glidants, lubricants, and the like. Typically, the carrier may be a solid (including powder), liquid, or combinations thereof. Each carrier is preferably "acceptable" in the sense of being compatible with the other ingredients in the composition and not injurious to the subject. The carrier is preferably biologically acceptable and inert, i.e., it permits the composition to maintain viability of the biological material until delivered to the appropriate site.

Oral compositions may include an inert diluent or an edible carrier. For the purpose of oral therapeutic administration, the active compound can be incorporated with excipients and used in the form of tablets, troches, or capsules, e.g., gelatin capsules. Oral compositions can also be prepared by combining a composition of the present invention with a food. In one embodiment a food used for administration is chilled, for instance, ice cream. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

The active compounds can also be prepared in the form of suppositories (e.g., with conventional suppository bases such as cocoa butter and other glycerides) or retention enemas for rectal delivery.

The active compounds may be prepared with carriers that will protect the compound against rapid elimination from the body, such as a controlled release formulation, including implants. Biodegradable, biocompatible polymers can be used, such as ethylene vinyl acetate, polyanhydrides, polyglycolic acid, collagen, polyorthoesters, and polylactic acid. Such formulations can be prepared using standard techniques. The materials can also be obtained commercially from, for instance, Alza Corporation and Nova Pharmaceuticals, Inc. Liposomal suspensions can also be used as pharmaceutically acceptable carriers. These can be prepared according to methods known to those skilled in the art.

In one embodiment, a composition may be encapsulated. For instance, when the composition is to be administered orally, the dosage form is formulated so the composition is not exposed to conditions prevalent in the gastrointestinal tract before the colon, e.g., high acidity and digestive enzymes present in the stomach and/or intestine. The encapsulation of compositions for therapeutic use is routine in the art. Encapsulation may include hard-shelled capsules, which may be used for dry, powdered ingredients soft-shelled capsules. Capsules may be made from aqueous solutions of gelling agents such as animal protein (e.g., gelatin), plant polysaccharides or derivatives like carrageenans and modified forms of starch and cellulose. Other ingredients may be added to a gelling agent solution such as plasticizers (e.g., glycerin and or sorbitol), coloring agents, preservatives, disintegrants, lubricants and surface treatment.

A composition may be prepared by obtaining a fecal sample from an appropriate donor and blending with a diluent. Useful diluents include aqueous solutions that are routinely used for manipulating microbes, eukaryotic cells, and/or viruses. Useful diluents may include constituents to maintain physiological buffer, osmolarity, and the like. The diluent is preferably sterile and/or non-allergenic. An example of a diluent includes, but is not limited to, phosphate buffered saline at pH 7. In one embodiment, 1 part donor feces may be combined with 5 parts diluent (e.g., 50 grams of donor feces may be combined with 250 mls diluent) and blended. In one embodiment, the oxygen in the blending chamber may be decreased or removed by purging with an inert gas such as nitrogen or argon prior to blending. Such anaerobic conditions may be useful to maintain viability of most anaerobic bacteria present in a colon. The sample may be blended multiple times and/or more diluent may be added until a consistency is achieved that will permit the following steps to occur. In one embodiment, anaerobic conditions are not used in steps following the blending. It was found that anaerobic conditions were not necessary in the steps following the blending, and this was unexpected and surprising since a substantial percentage of prokaryotic cells in fecal material are strict anaerobes, and exposure to oxygen kills them. After the blending, the solutions used for washing and resuspension did not need to be purged of oxygen, and manipulation of the microbiota in an oxygen-free cabinet or glove box was not needed.

Not all microbes and eukaryotic cells present in an individual's colon can be cultured, thus, in one embodiment conditions for preparing a composition include the use of temperatures that decrease the replication of the microbes and eukaryotic cells. In one embodiment, the conditions used for preparation are maintained below 37° C. For instance, the conditions used for preparation are maintained at a temperature of no greater than 30° C., no greater than 20° C., no greater than 10° C., or no greater than 5° C. In one embodiment, conditions are used such that replication of the microbes and eukaryotic cells does not occur. When the conditions used to prepare a composition of the present invention include lower temperatures to minimize replication and cell death, the biological material present in a composition includes a population of microbes, eukaryotic cells, and viruses that is essentially identical to a population of microbes, eukaryotic cells, and viruses present in the colon or feces of a normal healthy human, e.g., the donor from whom the fecal sample was obtained.

Removal of non-living material may be achieved by passing the blended sample through a sieve with a sieve size of no greater than 2.0 mm, no greater than 1.0 mm, no greater than 0.5 min, no greater than 0.25 mm, no greater than 0.212 mm, no greater than 0.180 mm, no greater than 0.150 mm, no greater than 0.125 mm, no greater than 0.106 mm, no greater than 0.090 mm, no greater than 0.075 mm, no greater than 0.063 mm, no greater than 0.053 mm, no greater than 0.045 mm, no greater than 0.038 mm, no greater than 0.032 mm, no greater than 0.025 mm, no greater than 0.020 nun, no greater than 0.01 mm, or no greater than 0.2 mm. In one embodiment, the blended sample is prepared by passing it through a sieve with a sieve size of 0.25 mm and collecting the filtrate. In one embodiment, the blended sample is passed through sieves with progressively smaller sieve sizes until final passage through a sieve size of 0.25 mm. For instance, if a total of four sieves are used the sieve size of the first sieve may be 2 mm, followed by 1 mm, followed by 0.5 mm, and then followed by 0.25 mm. The final filtrate may be collected in a centrifuge tube, and centrifuged at a speed sufficient to pellet the biological material, for instance, 10,000×g for 10 minutes at 4° C. The supernatant is removed, the cells are resuspended in diluent, optionally centrifuged again, for instance at 10,000×g for 10 minutes at 4° C. The final supernatant is discarded and the cells are resuspended in an aqueous solution (e.g., diluent, cryoprotectant, and the like, or a combination thereof). In one embodiment, the volume of the blended mixture is decreased through the steps of sieving and washing. For instance, in one embodiment, the volume is decreased to 14% of the volume used in the blending (e.g., from 250 mls to 35 mls). In one embodiment, the volume of the blended mixture is decreased through the steps of sieving and washing to result in between $1 \times 10^{10}$ and $5 \times 10^{10}$ cells in a volume that is subsequently administered to a subject. This process results in an extract of feces that is highly enriched for all colon microbiota that are able to pass through a sieve as described above, and can be centrifuged at 10,000×g for 10 minutes. As used herein, "enriched" refers to increasing the abundance of biological material relative to non-living material, such that biological material constitutes a significantly higher proportion compared to the fecal material before the enrichment. The term "enriched" refers to those situations in which a person has intervened to elevate the proportion of biological material.

The amount of aqueous solution added may be in an amount to result in a single dosage having an appropriate number of cells. In one embodiment, a single dosage may include between $1 \times 10^{10}$ and $5 \times 10^{10}$ cells, for instance, $3 \times 10^{10}$ cells. Since most biological material is difficult or impossible to culture, a hemocytometer may be used to determine the number of cells.

In one embodiment the resulting pellet may be suspended in half the original volume of diluent containing 10% glycerol. The sample may be used immediately, or may be frozen, for instance, at −80° C., for later use. When freezing, the sample may be left in a centrifuge tube, or may be in a different container. In one embodiment, the container is one that increases the surface area of the sample. For instance, the sample may be placed in an IV bag. When the frozen sample is to be used, it may be thawed on ice and then transplanted into the recipient. It was found that freezing the compositions described herein did not result in destruction of its curative potential. In one embodiment the sample resulting from centrifugation may be processed for long term storage of 1 year or longer. The ability to store such a sample provides a level of flexibility that was not possible with other methods. For instance, it was necessary to quickly identify a donor, rapidly process a fecal sample from the donor, and use it immediately. Examples of useful processing methods include, but are not limited to, freezing, freeze drying, spray drying, lyophilization, vacuum drying, air drying, or other forms of evaporative drying. Processing of a composition of the present invention may include the production of a powder following any drying procedure.

The use of sieves to extract biological material from fecal material unexpectedly resulted in a composition which was nearly odorless. This was not expected because feces normally have a distinctive odor and this was surprising to be removed by the minimal manipulation used. This is a significant advantage as it takes a method that is unaesthetic and so distasteful that some patients and staff refuse to take part, and changes it into a method that is easily practiced in a normal clinical setting or at home. As used herein, "odorless" means there is a decreased amount of volatile organic molecules present, and the decreased amount of volatile organic molecules present can be easily detected by a person comparing the material before processing with the material after processing.

The present invention is further directed to methods of using the compositions described herein. A method of the present invention includes administering to a subject in need thereof an effective amount of a composition described herein. The administering is under conditions suitable for deposition of the composition in a region of the large or small intestine such that the biological material in the composition colonizes the colon. For instance, administration may be into upper gastrointestinal tract, as well as lower gastrointestinal tract, e.g., the terminal ileum, cecum, colonic areas containing diverticulosis, and rectum. In one embodiment the administering may be oral, such as by tablet. In one embodiment the administering may be by intubation, such as by nasogastric tube. In one embodiment the administering may be rectal, for instance by a colonoscope, enema, or suppository. Conditions that are "suitable" for an event to occur, or "suitable" conditions are conditions that do not prevent such events from occurring. Thus, these conditions permit, enhance, facilitate, and/or are conducive to the event. As used herein, an "effective amount" relates to a sufficient amount of a composition described herein, to provide the desired effect. For instance, in one embodiment an "effective amount" is an amount effective to alleviate one or more symptoms and/or signs of the disease as described herein. In some embodiments, an effective amount is an amount that is sufficient to effect a reduction in a symptom and/or sign associated with a disease, such as diarrhea or *C. difficile*. A reduction in a symptom and/or a sign is, for instance, at least 10%, at least 20%, at least 30%, at least 40%, at least 50%, at least 60%, at least 70%, at least 80%, at least 90%, or at least 100% in a measured sign as compared to a control, a non-treated subject, or the subject prior to administration of the composition. In one embodiment, an effective amount is an amount sufficient to result in at least $1\times10^{10}$, at least $3\times10^{10}$, or at least $5\times10^{10}$ cells delivered to the colon. It will be understood, however, that the total dosage of the compositions as disclosed herein will be decided by the attending physician within the scope of sound medical judgment. The exact amount required will vary depending on factors such as the type and extent of disease being treated.

In one embodiment, a method of the present invention includes treating certain diseases in a subject in need of treatment. The subject may be a mammal, such as a human. In some embodiments animal models may be used, such as a mammal, including a rat, a mouse, a hamster, a gerbil, or a primate. As used herein, the term "disease" refers to any deviation from or interruption of the normal structure or function of a part, organ, or system, or combination thereof, of a subject that is manifested by a characteristic symptom or clinical sign. Diseases include those characterized by dysfunctional composition of colon microbiota. Such diseases include, but are not limited to, colitis, including autoimmune colitis (e g, inflammatory bowel disease, ulcerative colitis, Crohn's disease, irritable bowel syndrome) and infectious colitis. Examples of infectious colitis include, but are not limited to *Clostridium difficile* colitis (e.g., acute *C. difficile* colitis, relapsing *C. difficile* colitis, or severe *C. difficile* colitis) and enterohemorrhagic colitis (e.g., a colitis caused by *Shigella* spp. or *E. coli*). Other examples of diseases include, but are not limited to, chronic diarrhea; chronic constipation, metabolic syndrome and obesity, atopic diseases including asthma, eczema, eosinophilic disorders of the GI tract, systemic autoimmunity including rheumatoid arthritis, systemic lupus erythematosis, multiple sclerosis, etc., chronic pain disorders such fibromyalgia, chronic fatigue syndrome, neurodegenerative disorders, eating disorders, and malnutrition.

As used herein, the term "symptom" refers to subjective evidence of disease or condition experienced by the patient and caused by disease. As used herein, the term "clinical sign," or simply "sign," refers to objective evidence of a disease present in a subject. Symptoms and/or signs associated with diseases referred to herein and the evaluation of such signs are routine and known in the art. Typically, whether a subject has a disease, and whether a subject is responding to treatment, may be determined by evaluation of signs associated with the disease.

Treatment of a disease can be prophylactic or, alternatively, can be initiated after the development of a disease. Treatment that is prophylactic, for instance, initiated before a subject manifests signs of a disease, is referred to herein as treatment of a subject that is "at risk" of developing a disease. An example of a subject that is at risk of developing a disease is a person having a risk factor. An example of a risk factor for *Clostridium difficile* colitis is antibiotic therapy of the gastrointestinal tract. Treatment can be performed before, during, or after the occurrence of the diseases described herein. Treatment initiated after the development of a disease may result in decreasing the severity of the signs of the disease, or completely removing the signs.

In one embodiment, a method of the present invention includes transplanting a microbiota from a donor to a recipient.

In one embodiment, a method of the present invention includes increasing the relative abundance of members of the phylum Firmicutes, such as a nonpathogenic member of the class Clostridia, and/or members of the phylum Bacteroidetes, in a recipient's colon. The phrase "relative abundance" refers to number of members of a phylum or class compared to the number of members of all other taxa in a recipient's colon. Such a comparison can be expressed as a percent. In one embodiment, the relative abundance of non-pathogenic members of the class Clostridia in a recipient's colon after the administration may be increased by at least 5%, at least 10%, at least 20%, or at least 50%, compared to the recipient's colon before the administration. In one embodiment, the relative abundance of members of the phylum Firmicutes in a recipient's colon after the administration may be increased by at least 5%, at least 10%, at least 20%, or at least 50% compared to the recipient's colon before the administration. The change in the abundance may be determined at, for instance, 3 days, 10 days, 15 days, or 25 days after the administration of fecal microbiota.

In one embodiment, a method of the present invention includes decreasing the relative abundance of members of the phylum Proteobacteria in a recipient's colon. In one embodiment, the relative abundance of members of the phylum Proteobacteria in a recipient's colon after the administration may be decreased by at least 10%, at least 20%, at least 30%, or at least 40% compared to the recipient's colon before the administration. The change in the abundance of members of the phylum Proteobacteria may be determined at, for instance, 3 days, 10 days, 15 days, or 25 days after the administration.

In one embodiment, the existing microbiota does not need to be cleared prior to administration of a composition of the present invention. In other embodiments clearance of the microbiota may be necessary. Methods for clearance of existing microbiota are known and routine. In one example, clearance can be accomplished by administering a cocktail of antibiotics for one week until a day prior to transplant. An example of a useful cocktail is Metronidazole (1000 mg twice daily), Rifaximin (550 mg twice daily), Vancomycin (500 mg twice daily), and Neomycin (1000 mg twice daily).

The present invention is illustrated by the following examples. It is to be understood that the particular examples, materials, amounts, and procedures are to be interpreted broadly in accordance with the scope and spirit of the invention as set forth herein.

Example 1

*Clostridium difficile* associated disease is a major known complication of antibiotic therapy. The pathogen is normally held in check by native colon microbiota, but this level of protection may be lost when these microbial communities are suppressed by antibiotics. Antibiotics used to treat *C. difficile* infection may also perpetuate its recurrence by continued suppression of normal microbiota. Thus, a significant fraction of patients suffer from recalcitrant *C. difficile* infection, and recalcitrant *C. difficile* infection is associated with significant morbidity. Fecal bacteriotherapy is an increasingly used method used to break the cycle of *C. difficile* infection recurrence presumably through restoration of normal intestinal microbial communities. We previously reported, in one clinical case, that bacteriotherapy of colon microbiota resulted in the replacement of a host's microbiota by that of the donor (Khoruts, et al., 2010, J. Clin. Gastroenterol., 44(5):354). In order to obtain a greater understanding of the composition and stability of microbial communities before and after bacteriotherapy, we have analyzed amplified 16S rRNA regions of fecal DNA (V5 and V6) by using a pyrosequencing technology (an Illumina HiSeq2000 or other Illumina platforms). Additional individuals are currently being processed and analyzed.

Introduction

*Clostridium difficile* is an emerging pathogen and the most common cause of nosocomial diarrhea.

Infections are often associated with antibiotic therapy, where the protective effect provided by the normal intestinal flora is disrupted.

*C. difficile* infection is often controlled by additional antimicrobial therapy, but approximately 20% of patients develop refractory disease resulting in recurrent diarrhea.

Bacteriotherapy, in the form of a fecal transplantation, has been shown to successfully treat refractory *C. difficile* infection.

Next generation sequencing technologies have allowed for a deeper interrogation of the intestinal microflora and was used in our study to examine changes in microbial community structure after transplantation.

Donor fecal material was obtained from the patient's son, who was tested for infectious disease, including *C. difficile*, Hepatitis A, B, or C viruses, HIV virus, *Salmonella, Campylobacter, Yersinia, Shigella, E. Coli* 0157:H7, *Helicobacter pylori, Treponema pallidum, Giardia,* and *Cryptosporidium.*

The patient was infused with donor fecal material by colonoscopy, which revealed severe, extensive diverticulosis in the sigmoid colon. The donor's fecal material was deposited into the cecum. Symptoms consistent with *C. difficile* infection were resolved within days of bacteriotherapy.

Methods

Patient fecal samples were collected at day −31 before the fecal transplant bacteriotherapy and at days 5, 21, 46, 95, 132, 159, 188, and 227 post transplantation. A donor fecal sample was collected the day of the procedure and deposited into the recipient's cecum.

DNA was extracted from fecal materials using a MOBIO ultra-clean fecal DNA kit (MOBIO Laboratories, Inc., Carlsbad, Calif.) as directed by the manufacturer. Triplicate samples were extracted and pooled.

The V6 hypervariable region of the bacteria 16S rRNA gene was amplified using 50 ng of extracted DNA as template. Barcoded primers were used for multiplex sequencing (Kysela et al., 2005, Environmental Microbiology 7:356-64, and Claesson et al., Nucleic Acids Research, 2010, Vol. 38, No. 22 e200 doi:10.1093/narigkq873). Triplicate samples were prepared and pooled.

Amplified samples were mixed in equimolar ratios and sequenced at the National Center for Genomic Research (NCGR) using the Illumina sequencing platform.

Figure 2:
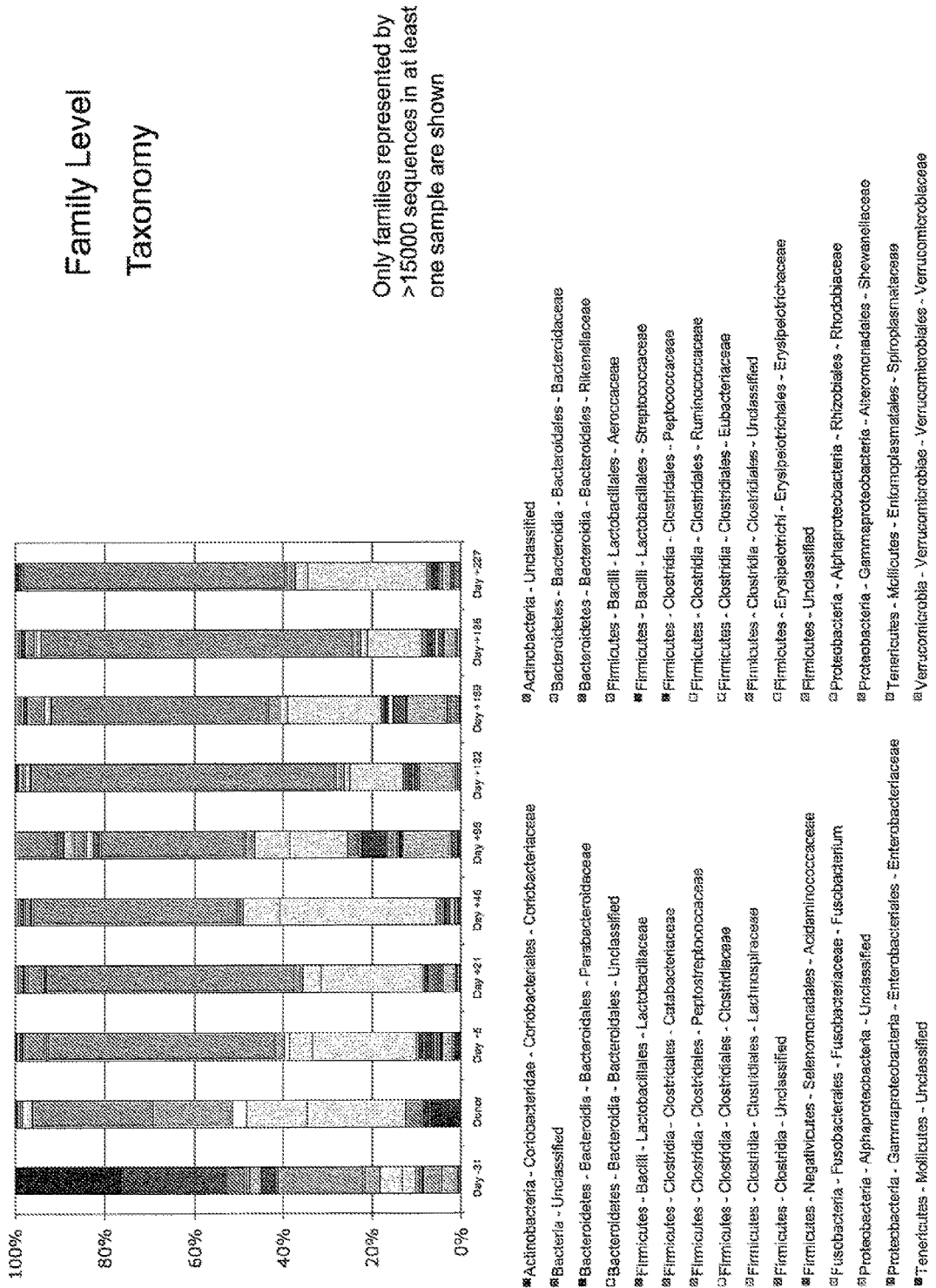
FIG. 2 is a plot of microbial community taxonomic distribution at the family level in a fecal transplant bacteriotherapy recipient before and after receiving the transplant in accordance with Example 1.

Sequence data was analyzed using MOTHUR and the SILVA reference database (Scholss, 2009, Appl. Environ. Microbiol., 75(23):7537-7541. The taxonomy of operational taxonomic units (OTUs) were assigned at the 97% similarity using the GreenGenes reference files. (FIGS. 1 and 2)

Figure 3:
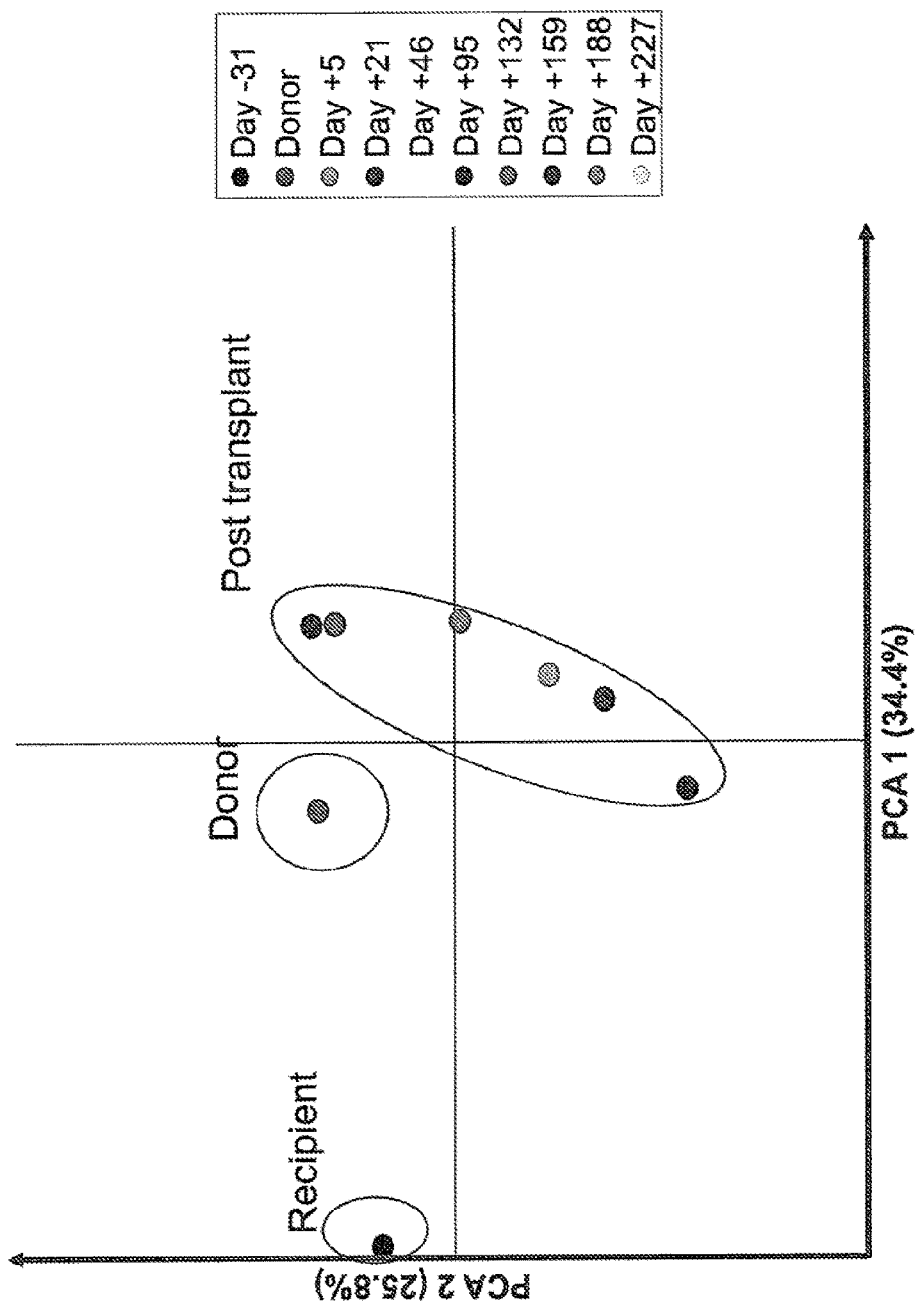
FIG. 3 is a plot of community analysis done using the Yue and Clayton's theta index showing that the post-transplantation samples from a recipient clustering closely with each other and with the donor's sample, compared to that of the recipient's pre-transplantation sample.

Principal component analysis was done using Yue and Clayton's Theta calculation (Yue and Clayton, 2005, Commun. Stat. Theor. Methods, 34:2123-2131). Accumulation curves were calculated based on 97% OTU similarities. (FIG. 3)

Results & Discussion

Greater than 40% of the sequences obtained from the recipient's pretransplantation sample (day −31) belonged to unclassified Mollicutes strains or the Gammaproteobacteria.

In contrast, the donor's and recipient's post-transplantation samples were dominated by Firmicutes. Unclassified members of the Clostridiales and the Ruminococcaceae family were abundant.

Community analysis done using the Yue and Clayton's theta index showed that the post-transplantation samples clustered more closely with each other and with the donor sample, compared to that of the recipient's pre-transplantation sample.

Sequence analysis indicated that the taxa present in the recipient's pre- and post-transplant fecal samples differed considerably, suggesting that fecal bacteriotherapy was successful in altering the patient's intestinal microflora.

The transplanted microbial community in the recipient's intestine remained fairly stable after 7.5 months post transplantation.

Surprisingly, sequences representing the Bacteroidales were in fairly low abundance in all of the samples analyzed.

TABLE 1

Pyrosequencing Metrics

| Sample Day | Seqs | OTUs (97%) | Coverage | Shannon Index |
|---|---|---|---|---|
| −31 | 1335704 | 15600 | 0.992 | 3.844 |
| Donor | 2892413 | 34945 | 0.992 | 4.663 |
| +5 | 2631872 | 28948 | 0.992 | 4.004 |
| +21 | 2909055 | 30038 | 0.993 | 4.047 |
| +46 | 3604923 | 35864 | 0.993 | 4.277 |
| +95 | 2216996 | 27782 | 0.991 | 4.631 |
| +132 | 2927800 | 26510 | 0.994 | 3.746 |
| +159 | 2691936 | 30990 | 0.992 | 4.551 |
| +188 | 1649565 | 18417 | 0.993 | 3.781 |
| +277 | 3073102 | 31162 | 0.993 | 3.852 |

Example 2

Donor Screening for Fecal Microbiota Material Preparation

The donor undergoes a complete medical history and physical examination. In addition, a full-length donor history questionnaire is completed as recommended by the FDA for blood donors, and potential donors saying yes to any of the questions are excluded (http://wwvv.fda.gov/downloads/BiologicsBloodVaccines/BloodBloodProducts/ApprovedProducts/LicensedProductsBLAs/BloodDonorScreening/UCM213552.pdf). However, as gut microbiota have been associated or postulated to be involved with multiple medical conditions, the process of selection is more rigorous than that of the blood donors and includes virtually any systemic illness.

Inclusion Criteria
1. Age >18
2. Ability to provide informed consent.

Exclusion Criteria
I. Medical History
  A. Risk of infectious agent.
    1. Known viral infection with Hepatitis B, C or HIV
    2. Known exposure to HIV or viral hepatitis at any time
    3. High risk behaviors including sex for drugs or money, men who have sex with men, more than one sexual partner in the preceding 12 months, any past use of intravenous drugs or intranasal cocaine, history of incarceration.
    4. Tattoo or body piercing within 12 months.
    5. Travel to areas of the world where risk of traveler's diarrhea is higher than the US.
    6. Current communicable disease, e.g., upper respiratory viral infection.
  B. Gastrointestinal comorbidities.
    1. History of irritable bowel syndrome. Specific symptoms may include frequent abdominal cramps, excessive gas, bloating, abdominal distension, fecal urgency, diarrhea, constipation.
    2. History of inflammatory bowel disease such as Crohn's disease, ulcerative colitis, microscopic colitis.
    3. Chronic diarrhea.
    4. Chronic constipation or use of laxatives.
    5. History of gastrointestinal malignancy or known colon polyposis.
    6. History of any abdominal surgery, e.g., gastric bypass, intestinal resection, appendectomy, cholecystectomy, etc.
    7. Use of Probiotics or any other over the counter aids used by the potential donor for purpose of regulating digestion. Yogurt and kefir products are allowed if taken merely as food rather than nutritional supplements.
  C. Factors that can or do affect the composition of the intestinal microbiota.
    1. Antibiotics for any indication within the preceding 6 months.
    2. Any prescribed immunosuppressive or anti-neoplastic medications.
  D. Systemic Medical Conditions.
    1. Metabolic Syndrome, established or emerging. Criteria used for definition here are stricter than any established criteria. These include history of increased blood pressure, history of diabetes or glucose intolerance.
    2. Known systemic autoimmunity, e.g., connective tissue disease, multiple sclerosis.
    3. Known atopic diseases including asthma or eczema.
    4. Chronic pain syndromes including fibromyalgia, chronic fatigue syndrome.
    5. Ongoing (even if intermittent) use of any prescribed medications, including inhalers or topical creams and ointments.
    6. Neurologic, neurodevelopmental, and neurodegenerative disorders including autism, Parkinson's disease.
II. Exclusion Criteria on Physical Examination.
1. General. Body mass index >26 kg/m$^2$, central obesity defined by waste:hip ratio >0.85 (male) and >0.80 (female).
2. Blood pressure >135 mmHg systolic and >85 mmHg diastolic.
3. Skin—presence of a rash, tattoos or body piercing placed within a year, jaundice.
4. Enlarged lymph nodes.
5. Wheezing on auscultation.
6. Hepatomegaly or *stigmata* of liver disease.
7. Swollen or tender joints. Muscle weakness.
8. Abnormal neurologic examination.

III. Exclusion Criteria on Laboratory Testing.
1. Positive stool *Clostridium difficile* toxin B tested by PCR.
2. Positive stool cultures for any of the routine pathogens including *Salmonella, Shigella, Yersinia, Campylobacter, E. coli* 0157:H7.
3. Abnormal ova and parasites examination.
4. Positive *Giardia, Cryptosporidium*, or *Helicobacter pylori* antigens.
5. Positive screening for any viral illnesses, including HIV 1 and 2, Viral Hepatitis A IgM, Hepatitis surface antigen and core Ab.
6. Abnormal RPR (screen for syphilis).
7. Any abnormal liver function tests including alkaline phosphatase, aspartate aminotransaminase, alanine aminotransferase.
8. Raised serum triglycerides >150 mg/dL
9. BDL cholesterol <40 mg/dL (males) and <50 mg/dL (females)
10. High sensitivity CRP >2.4 mg/L
11. Raised fasting plasma glucose (>100 mg/dL)

Example 3

Fecal Sample Processing

Donor fecal material is immediately chilled on ice for transport to the laboratory. Samples are processed within one hour after collection.

Fecal samples are homogenized by mixing 50 g of donor feces and 250 ml of sterile phosphate buffered saline, pH 7, (PBS) in a Waring Blender. The blending chamber is purged with nitrogen gas for several minutes to remove oxygen prior to homogenization. Samples are blended three times on the lowest setting for 20 seconds. Additional PBS or blending cycles may be added depending on the consistency of the fecal suspension. Blended samples are passed through a series of four sieves with pore sizes of 2.0 mm, 1.0 mm, 0.5 mm and 0.25 mm (W.S. Tyler Industrial Group, Mentor, Ohio). The sieves were based on US standard sieve sizes of 10, 18, 35, and 60 for 2.0 mm, 1.0 mm, 0.5 mm and 0.25 mm, respectively. The final filtrate passing through the sieves (less than 0.25 mm fraction) is collected in 50 ml conical centrifuge tubes and centrifuged at 4,000 rpm (about 4,000×g) for 10 minutes at 4° C. The supernatant is discarded and the pellet is suspended in one half the original volume of PBS (e.g. 125 ml) containing 10% glycerol. The samples are used immediately, or stored frozen at −80° C. and thawed on ice before transplantation.

Example 4

This example reports clinical experience with 43 consecutive patients that were treated for recurrent CDI *C. difficile* infection (CDI). During this time donor identification and screening was simplified by moving from patient-identified individual donors to standard volunteer donors. Material preparation shifted from the endoscopy suite to a standardized process in the laboratory, and ultimately to banking frozen processed fecal material that is ready to use when needed.

Standardization of material preparation significantly simplified the practical aspects of treatment without loss of apparent efficacy in clearing recurrent CDI. Approximately 30% of the patients had underlying inflammatory bowel disease, and treat went was equally effective in this group. Several key steps in standardization of donor material preparation significantly simplified the clinical practice of treatment of recurrent CDI in patients failing antibiotic therapy. This is also reported in Hamilton et al., Am. J. Gastroenterol., 2012, doi:10.1038/ajg.2011.482.

Methods

Patients

This report includes the first 43 patients who received fecal microbiota transplantation (FMT) for recurrent CDI. All patients were identified by direct referral from clinicians at infectious disease and gastroenterology practices in the Minneapolis and St. Paul metropolitan area. Inclusion criteria for FMT included a history of symptomatic, toxin-positive, infection by *C. difficile* and at least two documented subsequent recurrences despite use of standard antibiotic therapy. At least one failed antibiotic regimen had to include a minimum of a 6 week course of tapered or pulsed vancomycin dosage, or at least a one month vancomycin course followed by a minimum two week rifaximin "chaser." The only exclusion criteria in the protocol were age <18 and medical fragility from non-*C. difficile* problems resulting in life expectancy of <1 year. In the latter situation we advised patients that the best therapeutic option was an indefinite course of vancomycin. All patients gave informed consent for FMT via colonoscopy, recognizing relatively limited experience with this treatment approach and the intrinsic unknowns associated with its use. The Institutional Review Board at the University of Minnesota approved prospective collection of clinical outcome data, while recognizing this experience does not constitute a clinical trial, and as such was not designed to test the efficacy of FMT in comparison with any other therapeutic options.

Donor Identification and Screening

At the start of the program patients were asked to self-identify potential donors. These included mothers (n=2), daughters (n=1), sons (n=3), wives (n=1), husbands (n=1), and friends (n=2). Prior to recruitment, the donors were required to submit available medical records and have a separate medical history interview away from the recipient patient. The history included: assessment of infectious risk, including identification of known risk factors for HIV and Hepatitis, current communicable diseases, and recent travel to areas of the world with a higher prevalence of diarrheal illnesses. Additional absolute donor exclusion criteria included gastrointestinal co-morbidities and the use of antibiotics within preceding three months. Since gut microbiota are likely involved in various aspects of energy metabolism and the functioning of the immune system, the presence of features of metabolic syndrome, autoimmunity, or allergic diseases were treated as relative exclusion criteria. Donors provided separate informed consent to participate in the protocol, which included risks associated with laboratory screening. The donors underwent serologic testing for HIV and Hepatitis B and C, and stool testing that included screening for routine enteric pathogens, *C. difficile* toxin B, and examination for ova and parasites, and *Giardia* and *Cryptosporidium* antigens.

Given varying logistic difficulties in recruiting individual patient-identified donors, the lack of availability of donor materials when needed, and no evidence to suggest a clear therapeutic advantage of using a related versus unrelated donor (e.g., son or daughter versus friend or domestic partner), volunteer donors were recruited into the FMT program. The advantages of this change included removing the burden of donor identification from the patient, improving the efficiency and costs related to donor screening, a more consistent supply donor fecal microbiota, and the ability to impose extensive and stringent exclusion criteria on donor selection (Table 2). Two unpaid volunteer donors were recruited during this period, and one of them provided the majority of donated fecal material. Donor medical history was reviewed prior to every donation and complete laboratory screening, as described above, was done every 6 months.

TABLE 2

Donor exclusion criteria.

| Donor Exclusion Criteria | History and Physical Examination | Laboratory Screening |
|---|---|---|
| Risk of Infectious Agent | 1. Known HIV or Hepatitis B, C infection.<br>2. Known exposure to HIV or viral hepatitis at any time.<br>3. High risk behaviors including sex for drugs or money, men who have sex with men, more than one sexual partner in the preceding 12 months, history of incarceration, any past use of intravenous drugs or intranasal cocaine.<br>4. Tattoo or body piercing within 12 months.<br>5. Travel to areas of the world with increased risk of traveler's diarrhea.<br>6. Current communicable disease, e.g., upper respiratory tract viral infection. | 1. Ab for HIV 1 and 2.<br>2. Viral Hepatitis A IgM.<br>3. Hepatitis B surface Ag and core Ab.<br>4. HCV Ab.<br>5. RPR.<br>6. Stool cultures for enteric pathoges including *Salmonella*, *Shigella*, *Yersinia*, *Campylobacter*, *E. Colt* 0157:H7.<br>7. Ova and parasites examination.<br>8. Positive stool *Giardia*, *Cryptosporidium* and *Helicobacter pylori* antigens.<br>9. *Clostridium difficile* toxin B PCR.<br>10. Liver function tests including alkaline phosphatase, AST, ALT. |
| Gastrointestinal comorbidities | 1. History of irritable bowel syndrome, or any of the associated symptoms, including frequent abdominal cramps, excessive gas, bloating, abdominal distension, fecal urgency, diarrhea or constipation.<br>2. History of inflammatory bowel disease such as Crohn's disease, ulcerative colitis, lymphocytic colitis.<br>3. Chronic diarrhea.<br>4. Chronic constipation or use of laxatives.<br>5. History of gastrointestinal malignancy or known colon polyposis.<br>6. History of any abdominal surgery, e.g., gastric bypass, intestinal resection, appendectomy, cholecystectomy, etc.<br>7. Use of probiotics or any other over the counter aids for specific purposes of regulating digestion. | |
| Systemic Medical Conditions | 1. Established metabolic syndrome or any early features suggestive of its emergence. Body mass index >26 kg/m2, waste:hip ratio >0.85 (male) and >0.8 (female); BP >135 mmHg systolic and >85 mmHg diastolic.<br>2. Known systemic autoimmunity, e.g., connective tissue disease, multiple sclerosis, etc.<br>3. Known atopic diseases including asthma or eczema.<br>4. Chronic pain syndromes including fibromyalgia, chronic fatigue syndrome<br>5. Ongoing (even if intermittent) use of any prescribed medications, including inhalers or topical creams and ointments.<br>6. Neurologic, neurodevelopmental, and neurodegenerative disorders including autism, Parkinson's disease, etc.<br>7. Presence of a skin rash, wheezing on auscultation, lymphadenopathy, hepatomegaly or any stigmata of liver disease, swollen or tender joints, muscle weakness, abnormal neurological examination. | 1. Serum triglycerides (>150 mg/dL).<br>2. HDL cholesterol <40 mg/dL (males) and <50 mg/dL (females).<br>3. High sensitivity CRP >2.4 mg/L.<br>4. Fasting plasma glucose >100 mg/dL.<br>5. Liver function tests, including alkaline phosphatase, AST, ALT.<br>6. FANA. |

TABLE 2-continued

Donor exclusion criteria.

| Donor Exclusion Criteria | History and Physical Examination | Laboratory Screening |
|---|---|---|
| Additional factors known to affect the composition of intestinal microbiota | 1. Antibiotics for any indication within the preceding 6 months. | |

Donor Material Preparation

Individual patient-identified donors used in the early phase of the program came into the outpatient endoscopy center 1-2 h prior to the scheduled procedure.

The fecal material was collected in a toilet hat and processed in a dedicated bathroom separate from the procedure room. Approximately 50 gm of fecal material was placed into a standard commercial blender (Oster, Sunbeam Corp, Rye, N.Y.) and homogenized in 250 mL of sterile, nonbacteriostatic nominal saline. The slurry was then passed through stainless steel tea strainers to remove larger particles that could interfere with loading the syringes.

The material obtained from volunteer "universal" donors was transported on ice into the laboratory, where it was processed within two hours of collection. The material was weighed and homogenized in a commercial blender in a dedicated biological cabinet. The slurry was then passed through 2.0 mm, 1.0 mm, 0.5 mm, and 0.25 mm stainless steel laboratory sieves (W. S. Tyler, Inc., Mentor, Ohio) to remove undigested food and smaller particulate material. The resulting material passing through the 0.25 mm sieve was centrifuged at 6,000×g for 15 min in a Sorvall SS-34 rotor and resuspended to one half the original volume in nonbacteriostatic natural saline. The resulting concentrated fecal bacteria suspension was administered to the patient immediately or amended with sterile pharmaceutical grade glycerol (Sigma, St. Louis, Mo.) to a final concentration of 10%, and stored frozen at −80° C. for one to eight weeks until used. Thawing was done over 2-4 hours in an ice bath prior to the FMT procedure. The frozen preparation was diluted to 250 ml with nonbacteriostatic normal saline prior to infusion in the donor. This fecal material extract, whether fresh or frozen, was nearly odorless and of reduced viscosity, color, and texture relative to earlier material prepared in the endoscopy center. Filtration of donor material allowed for effortless loading of large tip 60 mL syringes without risk of clogging. All containers, bottles, and sieves used in material preparation were sterilized prior to use. Fecal material from universal donors was treated in the same manner as that obtained from patient-identified donors.

Transplantation Procedure

Patients were maintained on full dose of vancomycin (125 mg, 4 times daily, by mouth) until two days prior to the FMT procedure. The day before the procedure the patients were prepped using a split dosage polyethylene glycol purge (GoLYTELY or MoviPrep), which is standard in our endoscopy unit, prior to colonoscopies to wash out residual antibiotic and fecal material. The patients underwent a full colonoscopy under conscious sedation. Mucosal biopsies were taken to rule out lymphocytic colitis in absence of obvious inflammatory bowel disease. The majority of the prepared donor material (220-240 mL) was administered via the colonoscope's biopsy channel into the patient's terminal ileum and cecum. In some cases, however, a small portion (50 mL) was also instilled into colonic areas containing maximal diverticulosis. Recovery procedure was identical to that routinely used for standard colonoscopy patients. All patients were instructed to contact the endoscopist in case of symptom recurrence, were formally followed in clinic 1-2 months after the procedure. Clearance of CDI was defined by resolution of diarrhea and negative stool testing for *C. difficile* at 2 months following FMT. All patients in this protocol also participated in a study examining fecal bacterial community structure, which involved collection of fecal specimens on days 3, 7, 14 and 1, 3, 6, and 12 months after the procedure. The research staff collected these specimens from the patient's places of residence, providing additional opportunities for symptom follow-up.

Statistical Analysis

Non-categorical data were compared using unpaired Student's t-test. Categorical data were compared using Fisher's exact test. GraphPad Prism software was used to calculate two-tailed and two-sided p-values that were calculated with each test, respectively.

Results

Demographics

The group of patients with recurrent CDI described in this report clearly had refractory disease as evidenced by the average number of sequential relapses and duration of the condition (Table 3). Furthermore, many patients had multiple risk factors for high probability of recurrence, such as history of severe CDI as evidenced by hospitalization, frequent use of non-*C. difficile* intercurrent antibiotics, and advanced age (Hu et al. Gastroenterology 2009; 136:1206-14). All patients failed a long taper or pulsed regimen of vancomycin, and 40% of patients also failed an additional long course of vancomycin followed by a two-week rifaximin "chaser" regimen. One of these patients also failed a 4-week course of rifaximin. Several patients (3/43) took 2-4 week course of nita7oxanide, which also failed to clear the infection. Patients with inflammatory bowel disease were not excluded from the protocol. Thirty five percent of our patients (14 of 40) had underlying IBD, including Crohn's disease (6/14), ulcerative colitis (4/14), and lymphocytic colitis (4/14). The patients with IBD were generally younger (Table 4), but did not differ in the refractory nature of CDI or severity of presentation than older patients. However, the majority of patients without underlying IBD had moderate to severe diverticulosis.

TABLE 3

Demographics of patient population. The first 10 cases were done using patient-identified individual donors. After that, the protocol shifted to use of a standard donor. Fresh material was used in the earlier cases, and later practice shifted to use of frozen material.

| Donor Material | Age (Mean ± SD) | Female Gender | Duration (months) of RCDI (Mean ± SD) | Number of Relapses (Mean ± SD) | History of Hospitalization for CDI | Interim Antibiotics | PPI | CRI | IBD | Diverticulosis | Success Rate |
|---|---|---|---|---|---|---|---|---|---|---|---|
| Individual Donor (n = 10) | 61 ± 22 | 70% | 12.7 ± 7.3 | 6.2 ± 3.0 | 70% | 60% | 60% | 30% | 30% | 50% | 7/10 (70%) |
| Standard Donor, Fresh Material (n = 12) | 55 ± 22 | 83% | 13.1 ± 9.8 | 6.4 ± 3.3 | 75% | 42% | 33% | 25% | 50% | 50% | 11/12 (92%) |
| Standard Donor, Frozen Material (n = 12) | 59 ± 21 | 67% | 10.1 ± 10.0 | 5.2 ± 3.0 | 38% | 43% | 43% | 14% | 24% | 48% | 19/21 (90%) |
| Total Experience | 59 ± 21 | 72% | 12.2 ± 10.3 | 5.9 ± 3.3 | 56% | 48% | 47% | 21% | 33% | 49% | 37/43 (86%) |

RCDI = Recurrent *C. difficile* Infection
PPI = Proton Pump Inhibitor medication
CRI = Chronic Renal Insufficiency or Failure
IBD = Inflammatory Bowel Disease

TABLE 4

Comparison of patients without and with underlying IBD. Definition of IBD includes patients with Crohn's disease, ulcerative colitis, and incidentally discovered lymphocytic colitis.

| | Non-IBD (n = 29) | IBD (n = 14) | p Value |
|---|---|---|---|
| Age (Mean ± SEM) | 64.7 ± 3.3 | 44.6 ± 5.8 | p = 0.0021 |
| Female | 69% | 79% | p = 0.43 (NS) |
| Duration of RCDI (Mean # of months ± SD) | 13.5 ± 2.1 | 8.3 ± 3.3 | 0 = 0.09 (NS) |
| Number of Relapses ± SD | 6.2 ± 3.0 | 4.4 ± 1.3 | p = 0.04 |
| Rate of Hospitalization | 55% | 57% | P = 1.00 (NS) |
| Interim Antibiotics | 51% | 36% | p = 0.35 (NS) |
| PPI | 48% | 43% | p = 1.00 (NS) |
| Renal Insufficiency | 32% | 14% | p = 0.69 NS) |
| Diverticulosis | 69% | 14% | p = 0.0028 |

Response to Treatment

The overall rate of infection clearance was 86% in response to a single infusion of donor fecal material, as evidenced by symptom resolution and negative PCR testing for *C. difficile* toxin B after two months of follow-up (Table 3). Negative testing for *C. difficile* toxin B for two months was accepted as therapeutic success in patients with underlying IBD, even in absence of complete symptom resolution. Three of ten patients (30%) who received FMT using material from patient-identified individual donors had a recurrence of CDI. Two standard donors were employed for the remaining 33 cases in this series, but the majority (30/33) were done using material prepared from a single donor. Three of 33 patients who received FMT from a standard donor (fresh or frozen) had a recurrence of CDI. The difference in donor source, patient-identified versus standard, was not significant (p=0.1270). There was no significant difference in clearing the infection with fresh (11/12) or frozen (19/21) donor material. All 6 patients who experienced recurrence of CDI after FMT were offered a repeat procedure. Two of these patients, both >80 years of age, had multiple other active medical problems and preferred to remain on indefinite treatment with vancomycin. Four other patients were treated with a second infusion, and all cleared the infection bringing the overall success rate to 95% (41 of 43 patients). All second infusions were performed using the standard donor derived material. One of the recurrences of CDI occurred in a patient who received his first infusion from the second standard donor. The same donor source was used for his second FMT. Three of the four patients who received a second FMT had underlying IRD; two patients had Crohn's disease and one had lymphocytic colitis. Finally, the fourth patient had a partial colon resection done for a stricture that developed following her initial CDI episode. She has a colostomy draining her proximal colon and a long segment of residual distal colon. After recurrence of CDI within three weeks following her first FMT we thought it was likely that engraftment in this case was complicated by difficulty in retaining the donor material due to high flow of fecal contents and relatively small size of the infected colon. The second infusion in this case was done with two doses of frozen standard donor material: one via the colostomy into the colon and the other into the jejunum using upper push enteroscopy. *C. difficile* testing of her fecal material was done weekly in the first month and monthly thereafter. No *C. difficile* was found over three months of follow-up.

No serious adverse events were noted following FMT in any of the patients, with ether fresh or frozen materials. A minority of patients (approximately a third) noted some irregularity of bowel movements and excessive flatulence during the first couple weeks following the procedure, but these symptoms resolved by the time they were seen in clinic follow-up. Enhanced colitis activity in patients with underlying IBD was not observed and there was improvement in overall colitis activity in all patients with UC, although that is easily attributable to clearing the CDI. Interestingly, all diagnoses of lymphocytic colitis were made for the first time from biopsies taken during the colonoscopies performed at the time of FMT. These patients completely normalized their bowel function and had no diarrhea after FMT without any additional medical therapy for lymphocytic colitis. Follow-up biopsies were not performed in these patients when they became asymptomatic.

Discussion

Recurrent infection is one of the most difficult clinical challenges in the spectrum of *C. difficile* induced diarrheal disease. The risk of recurrence increases up to 65% after two or more episodes (McDonald et al. Emerg Infect Dis 2006; 12:409-15), and this risk is nearly certain in older patients who suffered severe CDI and suffered additional disruption of gut microbiota from intercurrent administration of non-*C. difficile* suppressing antibiotics (Hu et al. Gastroenterology 2009; 136:1206-14). The inclusion criteria for patients in this case series were simple: at least three recurrences and failure of standard antibiotic treatments. Our patients averaged about six recurrences over an average course of one year. This population highlights known risk factors for recurrence of CDI other than documented recurrence. The majority had history of at least one hospitalization for severe CDI and almost half took antibiotics after developing CDI for another non-*C. difficile* indication. Patients with inflammatory bowel disease dominated the younger age group. Virtually all patients were taking probiotics at presentation and many have also tried toxin-binding resins. We did not systematically collect information on all the various probiotics preparations taken by our patients, and many have tried multiple types through the course of their recurrent infections. The most common preparations contained *Saccharomyces boulardii* and strains of Lactobacilli. All patients were recommended to discontinue taking probiotics after FMT. In summary, by all available indicators the patients in this case series had recalcitrant CDI that would not have had a significant response rate to a placebo, and were unlikely to respond to another course of antibiotics or other available therapeutic options.

FMT has been used for decades as a last ditch method to cure recurrent CDI, and there has been growing uncontrolled evidence supporting its efficacy. Here we report one of the largest single case series. The 95% overall success rate in this series is comparable to the cumulative experience in the literature (Bakken. Anaerobe 2009; 15:285-9, van Nood et al. Euro Surveill 2009; 14, Khoruts and Sadowsky. Mucosal Immunol 2011; 4:4-7), and adds to the impetus for developing this therapeutic approach to make it more widely available. The major issues tackled by our center were those of practicality. In the early phase of the program we asked the patients to bring in prospective donors, which is the most common approach in practice at this time. Our experience does not contradict the efficacy of this approach. However, donor identification and work-up increased expense of the procedure and introduced a potential delay period. Moreover, some patients who were already exhausted by the illness had difficulty in finding suitable donors. While the ideal state of donor health may not be essential for elderly recipients with limited life expectancy, we felt compromise was not an option for younger patients on any of the donor exclusion criteria. Gut microbiota constitute a human microbial organ with major functions in energy metabolism and function of the immune system (Khoruts and Sadowsky. Mucosal Immunol 2011; 4:4-7). Therefore, this transplant procedure has potential implications for systemic physiology of the recipient. While donor health is not a guarantee to optimal composition of gut microbiota, it is currently the only available indicator. For all these reasons we decided to introduce the standard donor option to our patients. Interestingly, although many patients came into clinic with some potential donor already identified, they all immediately preferred the standard option of an anonymous screened donor upon learning about it.

The next challenge became advance preparation of the donor material. Little is known about viability of different constituents of fecal microbiota over time, and we did not wish to test this variable. However, since production of fresh material on demand is not always practical, and does create delay and issues of sanitation and aesthetics, we introduced frozen donor material as another treatment option. The clinical efficacy of frozen preparation became quickly evident and it has now become part of the standard protocol in our program.

FMT is typically considered a last choice, desperate therapy option by most clinicians, and to a great extent that is due to multiple aesthetic and practical barriers that stand in the way of its administration. Increased prevalence, morbidity, and mortality of CDI has now reached epidemic proportions and a significant fraction of these patients cannot clear the infection with standard therapies. These patients may benefit from FMT, but it is likely that the procedure is not available to them. Our FMT protocol has now progressed to the point where most obvious aesthetic and practical challenges have been overcome. This also significantly reduces costs associated with screening of potential donors. While effort and organization is required for recruitment and screening of suitable donors, as well as material preparation and banking, execution of actual FMT has become a simple matter of loading the syringes with thawed, nearly odorless, material and a colonoscopy.

There are a number of limitations to this study. It was not a rigorous clinical trial designed to test efficacy of a particular FMT methodology versus another, or some other form of therapy. Instead, it was an attempt to standardize FMT, as the procedure protocol evolved in the course of our clinical experience. Additional work is needed to ready this procedure for clinical trials and wider application. Nevertheless, our clinical outcomes provide very convincing evidence for efficacy of the frozen preparations. However, we cannot conclude from this experience alone that the fresh and frozen preparations are equivalent. The complexity of the donor material preparations, technical inability to culture most of the contained microbial constituents by classic laboratory techniques, and our ignorance as to the identity of species that are therapeutically most important precluded simple tests of donor material prior to FMT that could predict its efficacy. However, we are currently working to characterize the microbial composition of donor material and recipients' fecal samples collected over time by high throughput 16S rRNA gene sequencing. Results of these experiments should provide some means to compare different donor preparations. In addition, we are working to develop practical laboratory tests that will allow for further standardization of microbial composition of donor preparations.

While application of FMT for recurrent CDI has a long history, case reports suggest that it may also have a place in treatment of IBD and IBS (Bennet et al. Lancet 1989; 1:164, Borody et al. J Clin Gastroenterol 2003; 37:42-7, Andrews and Borody. Med J Aust 1993; 159:633-4). Given the potentially important role of gut microbiota in pathogenesis of the metabolic syndrome, FMT is already being explored in a clinical trial for this condition (Vrieze et al. Diabetologia 2010; 53:606-13). Simplification and standardization of FMT-based therapeutics is critical for its future development. Recent technological advances have also made it possible to gain insight into composition of gut microbiota and their activity. The study of microbiota in the context of FMT should accelerate development of microbial therapeutics and yield new insights into microbial host interactions.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. Supplementary materials referenced in publications (such as supplementary tables, supplementary figures, supplementary materials and methods, and/or supplementary experimental data) are likewise incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

What is claimed is:

1. A method of increasing the relative abundance of one or more members of the phylum Firmicutes in a patient in need thereof, the method comprising:
   administering to said patient an effective amount of a pharmaceutical composition comprising a human fecal microbe preparation comprising a pharmaceutically acceptable carrier and a human fecal extract comprising a healthy human fecal donor's intestinal microbiota comprising at least 6 different classes of bacteria selected from the group consisting of Actinobacteria, Bacteroidia, Bacilli, Clostridia, Erysipelotrichi, Alphaproteobacteria, Betaproteobacteria, Gammaproteobacteria, Mollicutes, and Verrucomicrobiae,
   wherein said human fecal extract comprises particles of nonliving material and particles of biological material, and said human fecal extract comprises no particle having a size of greater than 0.5 mm, and
   wherein the administering increases the relative abundance of total members of the phylum Firmicutes by at least 20% compared to before said administering.

2. The method of claim 1, wherein said administering increases the relative abundance of one or more members of the phylum Firmicutes by at least 20% compared to before said administering.

3. The method of claim 2, wherein said one or more members of the phylum Firmicutes are one or more non-pathogenic members of the class Clostridia.

4. The method of claim 3, wherein the relative abundance of said one or more non-pathogenic members of the class Clostridia is increased by at least 20% compared to before said administering.

5. The method of claim 1, wherein the relative abundance is determined at a time selected from the group consisting of 3 days after said administering, 10 days after said administering, 15 days after said administering, and 25 days after said administering.

6. The method of claim 1, wherein said administering is orally administering.

7. The method of claim 1, further comprising pretreating said patient with one or more antibiotics prior to said administering.

8. The method of claim 7, wherein said one or more antibiotics are selected from the group consisting of Metronidazole, Rifaximin, Vancomycin, and Neomycin.

9. The method of claim 1, wherein said human fecal donor is unrelated to said patient.

10. The method of claim 1, wherein said human fecal preparation consists essentially of particles capable of passing through a 0.5 mm sieve and the human fecal donor's intestinal microbiota.

11. The method of claim 1, wherein said pharmaceutical composition is frozen.

12. The method of claim 1, wherein said effective amount of said pharmaceutical composition comprises at least $5 \times 10^{10}$ cells.

13. The method of claim 1, wherein said patient has a *Clostridium difficile* infection.

14. The method of claim 13, wherein said administering also increases the fecal microbiota diversity in said patient compared to before said administering.

15. The method of claim 1, wherein said patient has a recurrent *Clostridium difficile* infection.

16. The method of claim 1, wherein said patient is at risk of developing a recurrent *Clostridium difficile* infection.

17. The method of claim 1, wherein said patient has an inflammatory bowel disease.

18. The method of claim 1, wherein said pharmaceutical composition is contained within a capsule.

19. The method of claim 1, wherein said administering is rectally administering.

20. The method of claim 1, wherein said pharmaceutical composition is lyophilized.

* * * * *